United States Patent [19]
Baker et al.

[11] Patent Number: 6,149,620
[45] Date of Patent: Nov. 21, 2000

[54] SYSTEM AND METHODS FOR ELECTROSURGICAL TISSUE TREATMENT IN THE PRESENCE OF ELECTRICALLY CONDUCTIVE FLUID

[75] Inventors: Michael A. Baker, Woodside; Stephen M. Brunell, Mountain View; Jean Woloszko, San Diego; Ronald A. Underwood, Belmont; Hira V. Thapliyal, Los Altos, all of Calif.; Philip E. Eggers, Dublin, Ohio

[73] Assignee: ArthroCare Corporation, Sunnyvale, Calif.

[21] Appl. No.: 09/248,763

[22] Filed: Feb. 12, 1999

Related U.S. Application Data

[63] Continuation of application No. 08/795,686, Feb. 5, 1997, Pat. No. 5,871,469, which is a continuation of application No. 08/561,958, Nov. 22, 1995, Pat. No. 5,697,882.
[60] Provisional application No. 60/096,150, Aug. 11, 1998, and provisional application No. 60/098,122, Aug. 27, 1998.

[51] Int. Cl.$^7$ .................................................. A61B 17/20
[52] U.S. Cl. .............................................................. 604/22
[58] Field of Search ............................. 604/22, 43, 48, 604/113, 114, 264, 271, 280; 607/27–32, 35, 38, 41

[56] References Cited

U.S. PATENT DOCUMENTS

| | | | |
|---|---|---|---|
| 2,050,904 | 8/1936 | Trice | 128/303 |
| 4,033,351 | 7/1977 | Hetzel | 128/303 |
| 4,040,426 | 8/1977 | Morrison, Jr. | 128/303 |
| 4,043,342 | 8/1977 | Morrison, Jr. | 128/303 |
| 4,116,198 | 9/1978 | Roos | 128/303 |

(List continued on next page.)

FOREIGN PATENT DOCUMENTS

| | | | |
|---|---|---|---|
| 0 703 461 A2 | 3/1996 | European Pat. Off. | G01R 27/02 |
| 0703461 | 3/1996 | European Pat. Off. | G01R 27/02 |
| 0 740 926 A2 | 11/1996 | European Pat. Off. | A61B 17/39 |
| 0740926 | 11/1996 | European Pat. Off. | A61B 17/39 |
| 0754437 | 1/1997 | European Pat. Off. | A61B 17/39 |

(List continued on next page.)

OTHER PUBLICATIONS

Rand et al. (1985) *J. Arthro. Surg.* 1:242–246. Effect of Electrocautery on Fresh Human Articular Cartilage.
C. Slager et al. (1987) *Z. Kardiologie* 76 (6) : 67–71.
C. Slager et al. (1985) *JACC* 5 (6) :1382–6.
P. Nardella (1989) *SPIE* 1068:42–49.
Elsasser et al. (1976) *Medizinal–Markt/Acta Medicotechnica* 24 (4) : 129–134.
E. Kramolowsky et al. (1991) *J. of Urology* 146 : 669–674.
R. Tucker et al. (1990) *Urol. Res.* 18 : 291–294.
R. Tucker et al. (1989) *J. of Urology* 141: 662–665.
R. Tucker et al. (1989) Abstract P14–11, 7$^{th}$ World Congress on Endourology and ESWL, Nov. 27–30, 1989, Kyoto, Japan.

*Primary Examiner*—John D. Yasko
*Assistant Examiner*—Manuel Mendez
*Attorney, Agent, or Firm*—John T. Raffle

[57] ABSTRACT

Systems and methods are provided for applying a high frequency voltage in the presence of an electrically conductive fluid to create a relatively low-temperature plasma for ablation of tissue adjacent to, or in contact with, the plasma. In one embodiment, an electrosurgical probe or catheter is positioned adjacent the target site so that one or more active electrode(s) are brought into contact with, or close proximity to, a target tissue in the presence of electrically conductive fluid. High frequency voltage is then applied between the electrode terminal(s) and one or more return electrode(s) to generate a plasma adjacent to the active electrode(s), and to volumetrically remove or ablate at least a portion of the target tissue. The high frequency voltage generates electric fields around the active electrode(s) with sufficient energy to ionize the conductive fluid adjacent to the active electrode(s). Within the ionized gas or plasma, free electrons are accelerated, and electron-atoms collisions liberate more electrons, and the process cascades until the plasma contains sufficient energy to break apart the tissue molecules, causing molecular dissociation and ablation of the target tissue.

22 Claims, 31 Drawing Sheets

U.S. PATENT DOCUMENTS

| | | | |
|---|---|---|---|
| 4,184,492 | 1/1980 | Meinke et al. | 128/303 |
| 4,202,337 | 5/1980 | Hren et al. | 128/303 |
| 4,228,800 | 10/1980 | Degler, Jr. et al. | 128/303 |
| 4,232,676 | 11/1980 | Herczog | 128/303 |
| 4,240,441 | 12/1980 | Khalil | 128/692 |
| 4,248,231 | 2/1981 | Herczog et al. | 128/303 |
| 4,326,529 | 4/1982 | Doss et al. | 128/303 |
| 4,381,007 | 4/1983 | Doss | 128/303 |
| 4,476,862 | 10/1984 | Pao | 128/303 |
| 4,532,924 | 8/1985 | Auth et al. | 128/303 |
| 4,548,207 | 10/1985 | Reimels | 128/303 |
| 4,567,890 | 2/1986 | Ohta et al. | 128/303 |
| 4,593,691 | 6/1986 | Lindstrom et al. | 128/303 |
| 4,658,817 | 4/1987 | Hardy | 128/303 |
| 4,674,499 | 6/1987 | Pao | 128/303 |
| 4,682,596 | 7/1987 | Bales et al. | 604/22 |
| 4,706,667 | 11/1987 | Roos | 128/303 |
| 4,709,698 | 12/1987 | Johnston et al. | 128/303 |
| 4,727,874 | 3/1988 | Bowers et al. | 128/303 |
| 4,765,331 | 8/1988 | Petruzzi et al. | 128/303 |
| 4,823,791 | 4/1989 | D'Amelio | 123/303 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,908 | 4/1991 | Rydell | 606/47 |
| 5,009,656 | 4/1991 | Reimels | 128/303 |
| 5,035,696 | 7/1991 | Rydell | 606/47 |
| 5,057,105 | 10/1991 | Malone et al. | 606/28 |
| 5,057,106 | 10/1991 | Kasevich et al. | 606/33 |
| 5,078,717 | 1/1992 | Parins et al. | 606/48 |
| 5,080,660 | 1/1992 | Buelna | 606/45 |
| 5,083,565 | 1/1992 | Parins | 128/642 |
| 5,098,431 | 3/1992 | Rydell | 606/48 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,156,151 | 10/1992 | Imran | 128/642 |
| 5,178,620 | 1/1993 | Eggers et al. | 606/41 |
| 5,190,517 | 3/1993 | Zieve et al. | 604/22 |
| 5,192,280 | 3/1993 | Parins | 606/48 |
| 5,195,959 | 3/1993 | Smith | 604/34 |
| 5,197,963 | 3/1993 | Parins | 606/46 |
| 5,217,457 | 6/1993 | Delahuerga et al. | 606/42 |
| 5,249,585 | 10/1993 | Turner et al. | 607/99 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,290,282 | 3/1994 | Casscells | 606/29 |
| 5,300,069 | 4/1994 | Hunsberger et al. | 606/37 |
| 5,312,400 | 5/1994 | Bales et al. | 606/41 |
| 5,314,406 | 5/1994 | Arias et al. | 604/21 |
| 5,318,563 | 6/1994 | Malis | 606/38 |
| 5,324,254 | 6/1994 | Phillips | 604/21 |
| 5,330,470 | 7/1994 | Hagen | 606/42 |
| 5,334,140 | 8/1994 | Phillips | 604/35 |
| 5,334,183 | 8/1994 | Wuchinich | 606/46 |
| 5,336,220 | 8/1994 | Ryan et al. | 604/22 |
| 5,336,443 | 8/1994 | Eggers et al. | 604/114 |
| 5,342,357 | 8/1994 | Nardella | 606/40 |
| 5,370,675 | 12/1994 | Edwards et al. | 607/101 |
| 5,380,277 | 1/1995 | Phillips | 604/33 |
| 5,380,316 | 1/1995 | Aita et al. | 606/7 |
| 5,383,876 | 1/1995 | Nardella | 606/49 |
| 5,383,917 | 1/1995 | Desai et al. | 607/702 |
| 5,389,096 | 2/1995 | Aita et al. | 606/15 |
| 5,395,312 | 3/1995 | Desai | 604/22 |
| 5,417,687 | 5/1995 | Nardella et al. | 606/32 |
| 5,419,767 | 5/1995 | Eggers et al. | 604/114 |
| 5,437,662 | 8/1995 | Nardella | 606/40 |
| 5,441,499 | 8/1995 | Fritzsch | 606/45 |
| 5,454,809 | 10/1995 | Janssen | 606/41 |
| 5,496,312 | 3/1996 | Klicek | 606/34 |
| 5,514,130 | 5/1996 | Baker | 606/41 |
| 5,554,152 | 9/1996 | Aita et al. | 606/7 |
| 5,556,397 | 9/1996 | Long et al. | 606/48 |
| 5,569,242 | 10/1996 | Lax et al. | 606/42 |
| 5,584,872 | 12/1996 | LaFontaine et al. | 607/116 |
| 5,609,151 | 3/1997 | Mulier et al. | 128/642 |
| 5,633,578 | 5/1997 | Eggers et al. | 323/301 |
| 5,647,869 | 7/1997 | Goble | 606/37 |
| 5,676,693 | 10/1997 | LaFontaine | 607/116 |
| 5,681,282 | 10/1997 | Eggers et al. | 604/114 |
| 5,683,366 | 11/1997 | Eggers et al. | 604/114 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,700,262 | 12/1997 | Acosta et al. | 606/48 |
| 5,725,524 | 3/1998 | Mulier et al. | 606/41 |
| 5,749,869 | 5/1998 | Lindenmeier et al. | 606/34 |
| 5,766,153 | 6/1998 | Eggers et al. | 604/114 |
| 5,807,395 | 9/1998 | Mulier et al. | 606/41 |
| 5,810,764 | 9/1998 | Eggers et al. | 604/23 |
| 5,843,019 | 12/1998 | Eggers et al. | 604/22 |
| 5,860,951 | 1/1999 | Eggers et al. | 604/49 |
| 5,860,974 | 1/1999 | Abele | 606/41 |
| 5,871,469 | 2/1999 | Eggers et al. | 604/114 |
| 5,873,855 | 2/1999 | Eggers et al. | 604/114 |
| 5,885,277 | 3/1999 | Korth | 606/35 |
| 5,888,198 | 3/1999 | Eggers et al. | 604/114 |
| 5,891,095 | 4/1999 | Eggers et al. | 604/114 |
| 5,897,553 | 4/1999 | Mulier et al. | 606/41 |
| 5,902,272 | 5/1999 | Eggers et al. | 604/114 |
| 5,944,715 | 8/1999 | Goble et al. | 606/41 |

FOREIGN PATENT DOCUMENTS

| | | | |
|---|---|---|---|
| 57-57802 | 4/1982 | Japan | A61B 1/100 |
| 57-117843 | 7/1982 | Japan | A61B 17/39 |
| 2 308 979 | 7/1997 | United Kingdom . | |
| 2 308 980 | 7/1997 | United Kingdom . | |
| 2 308 981 | 7/1997 | United Kingdom . | |
| 2327350 | 1/1999 | United Kingdom | A61B 17/39 |
| 2327351 | 1/1999 | United Kingdom | A61B 17/39 |
| 2327352 | 1/1999 | United Kingdom | A61B 17/39 |
| WO 90/07303 | 7/1990 | WIPO | A61B 17/39 |
| WO 92/21278 | 12/1992 | WIPO | A61B 5/04 |
| WO 93/13816 | 7/1993 | WIPO | A61B 17/36 |
| 93/20747 | 10/1993 | WIPO | A61B 5/00 |
| 94/04220 | 3/1994 | WIPO | A61N 1/06 |
| 94/08654 | 4/1994 | WIPO | A61M 37/00 |
| 95/34259 | 12/1995 | WIPO | A61F 5/48 |
| 96/00042 | 1/1996 | WIPO | A61B 17/39 |
| 97/00646 | 1/1997 | WIPO | A61B 17/39 |
| 97/00647 | 1/1997 | WIPO | A61B 17/39 |
| 97/24073 | 7/1997 | WIPO | A61B 17/39 |
| 97/24993 | 7/1997 | WIPO | A61B 17/39 |
| 97/24994 | 7/1997 | WIPO | A61B 17/39 |
| 97/48345 | 12/1997 | WIPO | A61B 17/39 |
| 97/48346 | 12/1997 | WIPO | A61B 17/39 |
| 98/27879 | 7/1998 | WIPO | A61B 17/36 |

BIOLING POINT OF WATER AT VARIOUS PRESSURES

Data based on the equation of state recommended by the International Association for the Properties of Steam in 1984, as presented in Haar, Gallagher, and Kell. "NBS-NRC Steam Tables" (Hemisphere Publishing Corp., New York, 1984). The temperature scale is IPTS-68.

Note that: 1mbar=100Pa=0.000986923 atoms=0.750062mmHg.

| P/mbar | T/°C  | P/mbar | T/°C  | P/mbar  | T/°C   | P/mbar | T/°C   |
|--------|-------|--------|-------|---------|--------|--------|--------|
| 50     | 32.88 | 915    | 97.17 | 1013.25 | 100.00 | 1200   | 104.81 |
| 100    | 45.82 | 920    | 97.32 | 1015    | 100.05 | 1250   | 105.99 |
| 150    | 53.98 | 925    | 97.47 | 1020    | 100.19 | 1300   | 107.14 |
| 200    | 60.07 | 930    | 97.62 | 1025    | 100.32 | 1350   | 108.25 |
| 250    | 64.98 | 935    | 97.76 | 1030    | 100.46 | 1400   | 109.32 |
| 300    | 69.11 | 940    | 97.91 | 1035    | 100.60 | 1450   | 110.36 |
| 350    | 72.70 | 945    | 98.06 | 1040    | 100.73 | 1500   | 111.38 |
| 400    | 75.88 | 950    | 98.21 | 1045    | 100.87 | 1550   | 112.37 |
| 450    | 78.74 | 955    | 98.35 | 1050    | 101.00 | 1600   | 113.33 |
| 500    | 81.34 | 960    | 98.50 | 1055    | 101.14 | 1650   | 114.26 |
| 550    | 83.73 | 965    | 98.64 | 1060    | 101.27 | 1700   | 115.18 |
| 600    | 85.95 | 970    | 98.78 | 1065    | 101.40 | 1750   | 116.07 |
| 650    | 88.02 | 975    | 98.93 | 1070    | 101.54 | 1800   | 116.94 |
| 700    | 89.96 | 980    | 99.07 | 1075    | 101.67 | 1850   | 117.79 |
| 750    | 91.78 | 985    | 99.21 | 1080    | 101.80 | 1900   | 118.63 |
| 800    | 93.51 | 990    | 99.35 | 1085    | 101.93 | 1950   | 119.44 |
| 850    | 95.15 | 995    | 99.49 | 1090    | 102.06 | 2000   | 120.24 |
| 900    | 96.71 | 1000   | 99.63 | 1095    | 102.19 | 2050   | 121.02 |
| 905    | 96.87 | 1005   | 99.77 | 1100    | 102.32 | 2100   | 121.79 |
| 910    | 97.02 | 1010   | 99.91 | 1150    | 103.59 | 2150   | 122.54 |

FIG. 30

| Elements | Compound | Concentration | Color |
|---|---|---|---|
| Sodium Chloride | NaCl | 0.1 mol dm3 | Orange-yellow |
| Barium Chloride | BaCl2 | 0.2 mol dm3 | Pale green |
| Strontium Chloride | SrCl2 | 0.2 mol dm3 | Bright red |
| Potassium Chloride | KCl | | Blue-purple |
| Potassium Nitrate | KNO3 | 0.2 mol dm3 | Violet |
| Copper Chloride | CuCl2 | 0.2 mol dm3 | Bright green-blue |
| Calcium Chloride | CaCl2 | 0.2 mol dm3 | Dull orange-red |
| Caesium Chloride | CsCl | 0.2 mol dm3 | Pale lilac |
| Lithium Chloride | LiCl | 0.2 mol dm3 | Bright pink-red |

SYSTEM AND METHODS FOR ELECTROSURGICAL TISSUE TREATMENT IN THE PRESENCE OF ELECTRICALLY CONDUCTIVE FLUID

RELATED APPLICATIONS

The present application derives priority from U.S. Provisional application Ser. Nos. 60/096,150 and 60/098,122, filed Aug. 11, 1998 and Aug., 27, 1998, respectively, con of U.S. patent application Ser. No. 08/795,686, now U.S. Pat. No. 5,871,469, filed Feb. 5, 1997, which is a continuation of U.S. Pat. No. 5,697,882, filed Nov. 22, 1995, the complete disclosures of which are incorporated herein by reference for all purposes.

The present invention is related to commonly assigned co-pending U.S. Patent Applications entitled "Systems and Methods for Treating Articular Cartilage", filed Oct. 23, 1998, Ser. No. 08/977,845, now pending, filed Nov. 25, 1997, which is a continuation-in-part of application Ser. No. 08/562,332,now U.S. Pat. No. 6,024,733 filed Nov. 22, 1995, and U.S. patent application Ser. No. 09/010,382, now pending, filed Jan. 21, 1998, the complete disclosure of which is incorporated herein by reference. The present invention is also related to commonly assigned co-pending U.S. patent application Ser. No. 09/162,117, now allowed filed Sep. 28, 1998, and U.S. Pat. No. 08/990,374, now allowed filed Dec. 15, 1997, which is a continuation-in-part of U.S. patent application Ser. No. 08/485,219, filed on Jun. 7, 1995, now U.S. Pat. No. 5,697,281, patent application Ser. Nos. 09/109,219, now pending, 09/058,571, now allowed, 08/874,173, now allowed, and 09/002,315, now pending, filed on Jun. 30, 1998, Apr. 10, 1998, Jun. 13, 1997, and Jan. 2, 1998, respectively, and U.S. patent application Ser. No. 09/054,323, filed on Apr. 2, 1998, now U.S. Pat. No. 6.063,079, and U.S. patent application Ser. No. 09/032,375, filed Feb. 27, 1998, now pending, Ser. No. 08/942,580, filed on Oct. 2, 1997, now allowed, U.S. application Ser. No. 08/753,227, filed on Nov. 22, 1996, now U.S. Pat. No. 5,873,855, U.S. application Ser. No. 08/687792, filed on Jul. 18, 1996, now U.S. Pat. No. 5,843,019, the complete disclosures of which are incorporated herein by reference for all purposes.

BACKGROUND OF THE INVENTION

The present invention relates generally to the field of electrosurgery and, more particularly, to surgical devices and methods which employ high frequency voltage to cut and ablate body tissue.

Conventional electrosurgical methods are widely used since they generally reduce patient bleeding associated with tissue cutting operations and improve the surgeon's visibility. These traditional electrosurgical techniques for treatment have typically relied on thermal methods to rapidly heat and vaporize liquid within tissue and to cause cellular destruction. In conventional monopolar electrosurgery, for example, electric current is directed along a defined path from the exposed or active electrode through the patient's body to the return electrode, which is externally attached to a suitable location on the patient's skin. In addition, since the defined path through the patient's body has a relatively high electrical impedance, large voltage differences must typically be applied between the active and return electrodes to generate a current suitable for cutting or coagulation of the target tissue. This current, however, may inadvertently flow along localized pathways in the body having less impedance than the defined electrical path. This situation will substantially increase the current flowing through these paths, possibly causing damage to or destroying tissue along and surrounding this pathway.

Bipolar electrosurgical devices have an inherent advantage over monopolar devices because the return current path does not flow through the patient beyond the immediate site of application of the bipolar electrodes. In bipolar devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue.

Another limitation of conventional bipolar and monopolar electrosurgery devices is that they are not suitable for the precise removal (i.e., ablation) or tissue. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. The tissue is parted along the pathway of evaporated cellular fluid, inducing undesirable collateral tissue damage in regions surrounding the target tissue site.

The use of electrosurgical procedures (both monopolar and bipolar) in electrically conductive environments can be further problematic. For example, many arthroscopic procedures require flushing of the region to be treated with isotonic saline, both to maintain an isotonic environment and to keep the field of view clear. However, the presence of saline, which is a highly conductive electrolyte, can cause shorting of the active electrode(s) in conventional monopolar and bipolar electrosurgery. Such shorting causes unnecessary heating in the treatment environment and can further cause non-specific tissue destruction.

Present electrosurgical techniques used for tissue ablation also suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 $\mu$m, frequently greater than 800 $\mu$m, and sometimes as great as 1700 $\mu$m. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

In an effort to overcome at least some of these limitations of electrosurgery, laser apparatus have been developed for use in arthroscopic and other surgical procedures. Lasers do not suffer from electrical shorting in conductive environments, and certain types of lasers allow for very controlled cutting with limited depth of necrosis. Despite these advantages, laser devices suffer from their own set of deficiencies. In the first place, laser equipment can be very expensive because of the costs associated with the laser light sources. Moreover, those lasers which permit acceptable depths of necrosis (such as excimer lasers, erbium:YAG lasers, and the like) provide a very low volumetric ablation rate, which is a particular disadvantage in cutting and ablation of fibrocartilage, articular cartilage, and meniscal tissue. The hohnium:YAG and Nd:YAG lasers provide much higher volumetric ablation rates, but are much less able to control depth of necrosis than are the slower laser devices. The $CO_2$ lasers provide high rate of ablation and low depth of tissue necrosis, but cannot operate in a liquid-filled cavity.

Excimer lasers, which operate in an ultraviolet wavelength, cause photodissociation of human tissue, commonly referred to as cold ablation. Through this mechanism, organic molecules can be disintegrated into light hydrocarbon gases that are removed from the target site. Such photodissociation reduces the likelihood of thermal damage to tissue outside of the target site. Although promising, excimer lasers must be operated in pulses so that ablation plumes created during operation can clear. This prevents excessive secondary heating of the plume of ablation products which can increase the likelihood of collateral tissue damage as well as a decrease in the rate of ablation. Unfortunately, the pulsed mode of operation reduces the volumetric ablation rate, which may increase the time spent in surgery.

SUMMARY OF THE INVENTION

The present invention provides systems, apparatus and methods for selectively applying electrical energy to body tissue. In particular, systems and methods are provided for applying a high frequency voltage in the presence of an electrically conductive fluid to create a relatively low-temperature plasma for ablation of tissue adjacent to, or in contact with, the plasma.

In one embodiment, the method of the present invention comprises positioning an electrosurgical probe or catheter adjacent the target site so that one or more active electrode(s) are brought into contact with, or close proximity to, a target tissue in the presence of electrically conductive fluid. The electrically conductive fluid may be delivered directly to the active electrode(s) and the target tissue, or the entire target site may be submersed within the conductive fluid. High frequency voltage is then applied between the electrode terminal(s) and one or more return electrode(s) to generate a plasma adjacent to the active electrode(s), and to volumetrically remove or ablate at least a portion of the target tissue. The high frequency voltage generates electric fields around the active electrode(s) with sufficient energy to ionize the conductive fluid adjacent to the active electrode(s). Within the ionized gas or plasma, free electrons are accelerated, and electron-atoms collisions liberate more electrons, and the process cascades until the plasma contains sufficient energy to break apart the tissue molecules, causing molecular dissociation and ablation of the target tissue.

In some embodiments, the high frequency voltage applied to the electrode terminal(s) is sufficient to vaporize the electrically conductive fluid (e.g., gel or saline) between the electrode terminal(s) and the tissue. Within the vaporized fluid, an ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,697,882.

In some embodiments, the tissue is ablating by directly contacting the target tissue with the plasma. In other embodiments, the active electrode(s) are spaced from the tissue a sufficient distance to minimize or avoid contact between the tissue and the plasma formed around the active electrode(s). Applicant believes that the electrons that carry the electrical current are hotter than the ions within the plasma. In these embodiments, contact between the heated electrons in the plasma and the tissue is minimized as these electrons travel from the plasma back through the conductive fluid to the return electrode(s). The ions within the plasma will have sufficient energy, however, under certain conditions such as higher voltages, to accelerate beyond the plasma to the tissue. Thus, the electrons, which are carried away from the target tissue, carry most of the thermal byproducts of the plasma with them, allowing the ions to break apart the tissue molecules in a substantially non-thermal manner.

In another embodiment, the method further includes the step of vaporizing the electrically conductive fluid near the active electrode(s) into a plasma at relatively low temperatures, preferably lower than about 100° C., more preferably lower than about 80° C. The lower temperature of the conductive fluid will further reduce any risk of undesired thermal damage to tissue surrounding the target site and provide an even more precise tissue removal. In one aspect of the invention, a reduced pressure environment is created around the active electrode(s) to lower the vaporization temperature of the conductive fluid. In other embodiments, the electrically conductive fluid itself has a relative low vaporization temperature (e.g., preferably below about 100° C. or below 80° C.) at atmospheric pressure.

In another aspect of the invention, the present invention provides methods and apparatus for increasing the energy level of the ionized plasma created at the end of the electrosurgical probe. According to the present invention, this is accomplished by altering the conductive fluid to either increase its conductivity or to increase the quantity or strength of the ions in the ionized plasma. In some embodiments, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

In yet another aspect of the invention, an electrically conductive fluid having a reduced ionic strength or a reduced conductivity is selected. Applicant has found that these conductive fluids may facilitate the initiation of the plasma layer in certain conditions, such as lower voltage levels or when a suction pressure is applied near the active electrode(s). In a specific configuration, saline solutions having concentrations less than isotonic saline (i.e., less than about 0.9% sodium chloride) are used to facilitate the initiation of the plasma layer, or to provide less aggressive ablation of tissue.

In a further aspect of the present invention, ionic particles contained in the electrically conductive fluid are selected to fluoresce specific colors as desired by the user when used with the electrosurgical probe. In preferred embodiments, the color of fluorescence is selected to simulate the color emitted by an excimer laser during ablation, e.g., blue or purple. Such color will provide certain psychological benefits to the user and patient during electrosurgery.

Apparatus according to the present invention generally include an electrosurgical instrument having a shaft with proximal and distal ends, one or more active electrode(s) at the distal end and one or more connectors coupling the active electrode(s) to a source of high frequency electrical energy. In some embodiments, the instrument will comprise a catheter designed for percutaneous and/or transluminal delivery. In other embodiments, the instrument will comprise a more rigid probe designed for percutaneous or direct delivery in either open procedures or port access type procedures. In both embodiments, the apparatus will include a high frequency power supply for applying a high frequency voltage to the electrode terminal(s).

The apparatus will further include a supply of electrically conductive fluid and a fluid delivery element for delivering electrically conducting fluid to the electrode terminal(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the target site. In this embodiment, the apparatus may not have a fluid delivery element. In both embodiments, the electrically conducting fluid will preferably generate a current flow path between the active electrode(s) and one or more return electrode(s). In an exemplary embodiment, the return electrode is located on the instrument and spaced a sufficient distance from the active electrode(s) to substantially avoid or minimize current shorting therebetween and to shield the return electrode from tissue at the target site.

The electrosurgical instrument will preferably include an electrically insulating electrode support member, preferably an inorganic support material (e.g., ceramic, glass, glass/ceramic, etc.) having a tissue treatment surface at the distal end of the instrument shaft. One or more electrode terminal (s) are coupled to, or integral with, the electrode support member such that the electrode terminal(s) are spaced from the return electrode. In one embodiment, the instrument includes an electrode array having a plurality of electrically isolated electrode terminals embedded into the electrode support member such that the electrode terminals extend about 0.0 mm to about 10 mm distally from the tissue treatment surface of the electrode support member. In this embodiment, the probe will further include one or more lumens for delivering electrically conductive fluid and/or aspirating the target site to one or more openings around the tissue treatment surface of the electrode support member. In an exemplary embodiment, the lumen will extend through a fluid tube exterior to the probe shaft that ends proximal to the return electrode.

In a specific configuration, the electrosurgical instrument includes an insulating member around the active electrode(s) that forms a plasma chamber adjacent to the active electrode (s). The insulating member preferably comprises an inorganic material, such as ceramic or glass, and it may comprise a transparent material that allows the physician to view the plasma formed therein. In some embodiments, the return electrode(s) are positioned exterior to the plasma chamber, proximally spaced on the instrument as described above. In other embodiments, the return electrode(s) may be positioned within the insulating member such that the electric currents are completely confined to the plasma chamber. In one configuration, the instrument further include a fluid lumen for delivering electrically conductive fluid to the plasma chamber, and a second fluid lumen for aspirating excess conductive fluid from the plasma chamber. The fluid lumens create a fluid recirculation system for minimizing the amount of conductive fluid that leaks onto the patient and for reducing the temperature of the conductive fluid in and around the plasma chamber.

BRIEF DESCRIPTION OF THE DRAWINGS

FIG. 30 is a chart listing the boiling temperature of water at varying pressures;

FIG. 32 lists the colors associated with the fluorescence of specific compounds.

DESCRIPTION OF SPECIFIC EMBODIMENTS

Figure 1:
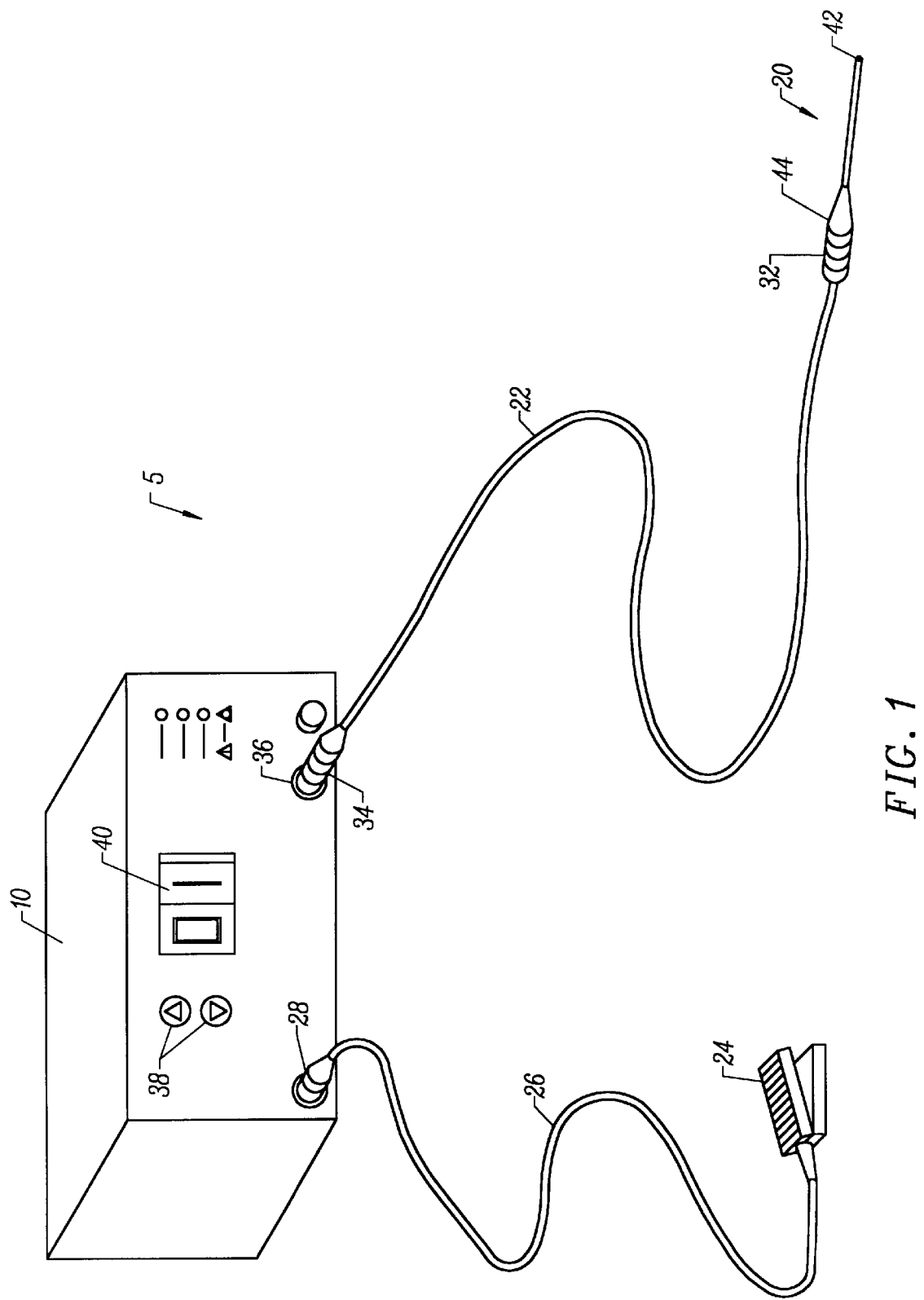
FIG. 1 is a perspective view of an electrosurgical system incorporating a power supply and an electrosurgical probe for treating articular cartilage according to the present invention.

In the present invention, high frequency (RF) electrical energy is applied to one or more electrode terminals in the presence of electrically conductive fluid to remove and/or modify body tissue. The techniques of the present invention may be performed in a conventional open surgery environment or in a minimally invasive manner using cannulas or port access devices. The present invention is useful in procedures where the tissue site is flooded or submerged with an electrically conducting fluid, such as arthroscopic surgery of the knee, shoulder, ankle, hip, elbow, hand or foot. Specifically, the present invention is useful in the resection and/or ablation of the meniscus and the synovial tissue within a joint during an arthroscopic procedure. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin. The present invention is also useful for resecting tissue within accessible sites of the body that are suitable for electrode loop resection, such as the resection of prostate tissue, leiomyomas (fibroids) located within the uterus and other diseased tissue within the body.

The present invention is particularly useful for treating tissue in the head and neck, such as the ear, mouth, pharynx, larynx, esophagus, nasal cavity and sinuses. The head and neck procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps, turbinates and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for collagen shrinkage, ablation and/or hemostasis in procedures for treating swollen tissue (e.g., turbinates) or snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies or the like.

The present invention may also be useful for treating tissue or other body structures in the brain or spine. These procedures include tumor removal, laminectomy/disketomy procedures for treating herniated disks, decompressive laminectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar diskectomies. These procedures may be performed through open procedures, or using minimally invasive techniques, such as thoracoscopy, arthroscopy, laparascopy or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, the remaining disclosure will be directed specifically to the treatment of tissue structures within a joint, e.g., arthroscopic surgery, but it will be appreciated that the system and method can be applied equally well to procedures involving other tissues of the body, as well as to other procedures including open procedures, intravascular procedures, interventional cardiology procedures, urology, laparascopy, arthroscopy, thoracoscopy or other cardiac procedures, cosmetic surgery, orthopedics, gynecology, otorhinolaryngology, spinal and neurologic procedures, oncology and the like. In one aspect of the invention, the body tissue is volumetrically removed or ablated. In this procedure, a high frequency voltage difference is applied between one or more electrode terminal (s) and one or more return electrode(s) to develop high electric field intensities in the vicinity of the target tissue. The high electric field intensities adjacent the electrode terminal(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid or gas, such as isotonic saline or blood, delivered to the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under the conditions described herein, induces the discharge of energetic electrons and photons from the vapor layer and to the surface of the target tissue. This energy may be in the form of energetic photons (e.g., ultraviolet radiation), energetic particles (e.g., electrons or ions) or a combination thereof. A more detailed description of this phenomena, termed Coblation™ can be found in commonly assigned U.S. Pat. No. 5,697,882 the complete disclosure of which is incorporated herein by reference.

Applicant believes that the principle mechanism of tissue removal in the Coblation™ mechanism of the present invention is energetic electrons or ions that have been energized in a plasma adjacent to the electrode terminal(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995). When the density of the vapor layer (or within a bubble formed in the electrically conducting liquid) becomes sufficiently low (i.e., less than approximately 1020 atoms/cm3 for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into fmal gaseous or liquid species.

Plasmas may be formed by heating a small of gas and ionizing the gas by driving an electric current through it, or by shining radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In some embodiments, the present invention applies high frequency (RF) electrical energy in an electrically conducting fluid environment to remove (i.e., resect, cut or ablate) a tissue structure and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal(s). In other embodiments, the power supply is combined with the coagulation instrument such that the coagulation electrode is used when the power supply is in the coagulation mode (low voltage), and the electrode terminal(s) are used when the power supply is in the ablation mode (higher voltage).

In one method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The present invention is also useful for removing or ablating tissue around nerves, such as spinal, or cranial nerves, e.g., optic nerve, facial nerves, vestibulocochlear nerves and the like. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode (s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue 4 surrounding nerves 6, the electrode terminals will shut off whenever they come in contact with, or in close proximity to, nerves. Meanwhile, the other electrode terminals, which are in contact with or in close proximity to nasal tissue, will continue to conduct electric current to the return electrode. This selective ablation or removal of lower impedance tissue in combination with the Coblation™ mechanism of the present invention allows the surgeon to precisely remove tissue around nerves or bone. Applicant has found that the present invention is capable of volumetrically removing tissue closely adjacent to nerves without impairment the function of the nerves, and without significantly damaging the tissue of the epineurium. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately 1020 atoms/cm3 for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into fmal gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998 (Attorney Docket No. CB-3), the complete disclosure of which is incorporated herein by reference.

The present invention also provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's brain or to the surgical staff. The high frequency voltage is preferably selected to effect controlled removal of these tissue cells while minimizing substantial tissue necrosis to surrounding or underlying tissue. A more complete description of this phenomena can be found in co-pending U.S. patent application Ser. No. 09/109, 219, filed Jun. 30, 1998 (Attorney Docket No. CB-1), the complete disclosure of which is incorporated herein by reference.

The electrosurgical instrument will comprise a shaft having a proximal end and a distal end which supports one or more electrode termiinal(s). The shaft may assume a wide variety of configurations, with the primary purpose being to mechanically support one or more electrode terminal(s) and permit the treating physician to manipulate the electrode(s) from a proximal end of the shaft. Usually, an electrosurgical probe shaft will be a narrow-diameter rod or tube, more usually having dimensions which permit it to be introduced through a cannula into the patient's body. Thus, the probe shaft will typically have a length of at least 5 cm for open procedures and at least 10 cm, more typically being 20 cm, or longer for endoscopic procedures. The probe shaft will typically have a diameter of at least 1 mm and frequently in the range from 1 to 10 mm. For dermatology or other procedures on the skin surface, the shaft will have any suitable length and diameter that would facilitate handling by the surgeon.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad). In most applications, applicant has found that it is preferably to have the return electrode on or near the shaft of the instrument to confine the electric currents to the target site. In some applications and under certain conditions, however, the invention may be practiced in a monopolar mode, with the return electrode attached to the external surface of the patient. Accordingly, the return electrode is preferably either integrated with the instrument shaft, or another instrument located in close proximity to the distal end of the instrument shaft. The proximal end of the instrument will include the appropriate electrical connections for coupling the return electrode(s) and the electrode terminal(s) to a high frequency power supply, such as an electrosurgical generator.

The current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal(s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998 (attorney Docket No. CB-4), the complete disclosure of which is incorporated herein by reference.

In some procedures, it may also be necessary to retrieve or aspirate the electrically conductive fluid and/or the non-condensible gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode (s) can be found in commonly assigned, co-pending patent application entitled "Systems And Methods For Tissue Resection, Ablation And Aspiration", filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be more precisely controlled, for example, by the use of a multiplicity of small electrode terminals whose effective diameters or principal dimensions range from about 10 mm to 0.01 mm, preferably from about 2 mm to 0.05 mm, and more preferably from about 1 mm to 0.1 mm. Electrode areas for both circular and non-circular terminals will have a contact area (per electrode terminal) below 50 mm2 for electrode arrays and as large as 75 mm2 for single electrode embodiments. In multiple electrode arrays, the contact area of each electrode terminal is typically in the range from 0.0001 mm2 to 1 mm2, and more preferably from 0.001 mm2 to 0.5 mm2. The circumscribed area of the electrode array or electrode terminal is in the range from 0.25 mm2 to 75 mm2, preferably from 0.5 mm2 to 40 mm2. In multiple electrode embodiments, the array will usually include at least two isolated electrode terminals, often at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor layer and subsequent plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

In other embodiments, the active electrodes are spaced from the tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

The electrically conducting fluid should have a threshold conductivity to provide a suitable conductive path between the return electrode and the electrode terminal(s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400–600 kHz) to minimize low frequency current flow into the heart or the nerves of the head and neck. The RMS (root mean square) voltage applied will usually be in the range from about 5 volts to 1000 volts, preferably being in the range from about 10 volts to 500 volts, often between about 150 to 350 volts depending on the electrode terminal size, the operating frequency and the operation mode of the particular procedure or desired effect on the tissue (i.e., contraction, coagulation, cutting or ablation). Typically, the peak-to-peak voltage for ablation or cutting with a square wave form will be in the range of 10 to 2000 volts and preferably in the range of 100 to 1800 volts and more preferably in the range of about 300 to 1500 volts, often in the range of about 300 to 800 volts peak to peak (again, depending on the electrode size, the operating frequency and the operation mode). Lower peak-to-peak voltages will be used for tissue coagulation or collagen contraction and will typically be in the range from 50 to 1500, preferably 100 to 1000 and more preferably 120 to 400 volts peak-to-peak (again, these values are computed using a square wave form) Higher peak-to-peak voltages, e.g., greater than about 700 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 to 600 kHz may be used in certain procedures in which stray low frequency currents may be problematic. A description of one suitable power source can be found in co-pending patent application Ser. Nos. 09/058,571 and 09/058,336, filed Apr. 10, 1998 (Attorney Docket Nos. CB-2 and CB-4), the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter or probe comprises a single active electrode terminal that extends from an insulating member, e.g., ceramic, at the distal end of the shaft. The insulating member is preferably a tubular structure that separates the active electrode terminal from a tubular or annular return electrode positioned proximal to the insulating member and the active electrode. In another embodiment, the catheter or probe includes a single active electrode that can be rotated relative to the rest of the catheter body, or the entire catheter may be rotated related to the lead. The single active electrode can be positioned adjacent the abnormal tissue and energized and rotated as appropriate to remove this tissue.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode.

Referring to FIG. 1, an exemplary electrosurgical system 5 for treatment of tissue in the body will now be described in detail. Electrosurgical system 5 is generally useful for minimally invasive procedures within the body, wherein a surgical instrument is introduced through a percutaneous penetration, or through a natural opening in the patient. As shown, electrosurgical system 5 generally includes an electrosurgical probe 20 connected to a power supply 10 for providing high frequency voltage to one or more electrode terminals 42 on probe 20. Probe 20 includes a connector housing 44 at its proximal end, which can be removably connected to a probe receptacle 32 of a probe cable 22. The proximal portion of cable 22 has a connector 34 to couple probe 20 to power supply 10. Power supply 10 has an operator controllable voltage level adjustment 38 to change the applied voltage level, which is observable at a voltage level display 40. Power supply 10 also includes one or more foot pedal(s) 24 and one or more cable(s) 26 which are each removably coupled to receptacle 30 with a cable connector 28. The foot pedal(s) 24 may include a second pedal (not shown) for remotely adjusting the energy level applied to electrode terminals 104, and a third pedal (also not shown) for switching between an ablation mode and a sub-ablation mode (such as coagulation or contraction).

In an exemplary embodiment, a first foot pedal 24 is used to place the power supply into the "ablation" mode and second foot pedal (not shown) places power supply 28 into the "coagulation" mode. The third foot pedal (not shown) allows the user to adjust the voltage level within the "ablation" mode. In the ablation mode, a sufficient voltage is applied to the electrode terminals to establish the requisite conditions for molecular dissociation of the tissue (i.e., forming a plasma with sufficient energy to ablate tissue). As discussed above, the requisite voltage level for ablation will vary depending on the number, size, shape and spacing of the electrodes, the distance in which the electrodes extend from the support member, etc. When the surgeon is using the power supply in the "ablation" mode, voltage level adjustment 40 or third foot pedal may be used to adjust the voltage level to adjust the degree or aggressiveness of the ablation. Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to one or more electrode terminals (or one or more coagulation electrodes) to avoid vaporization of the electrically conductive fluid, formation of a plasma and subsequent molecular dissociation of the tissue. The surgeon may automatically toggle the power supply between the ablation and coagulation modes by alternatively stepping on the appropriate foot pedals. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on the appropriate foot pedal, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on the appropriate foot pedal A specific design of a suitable power supply for use with the present invention can be found in U.S. patent application Ser. No. 09/058,571, filed Apr. 10, 1998 (attorney docket no. CB-2), previously incorporated herein by reference.

Figure 2:
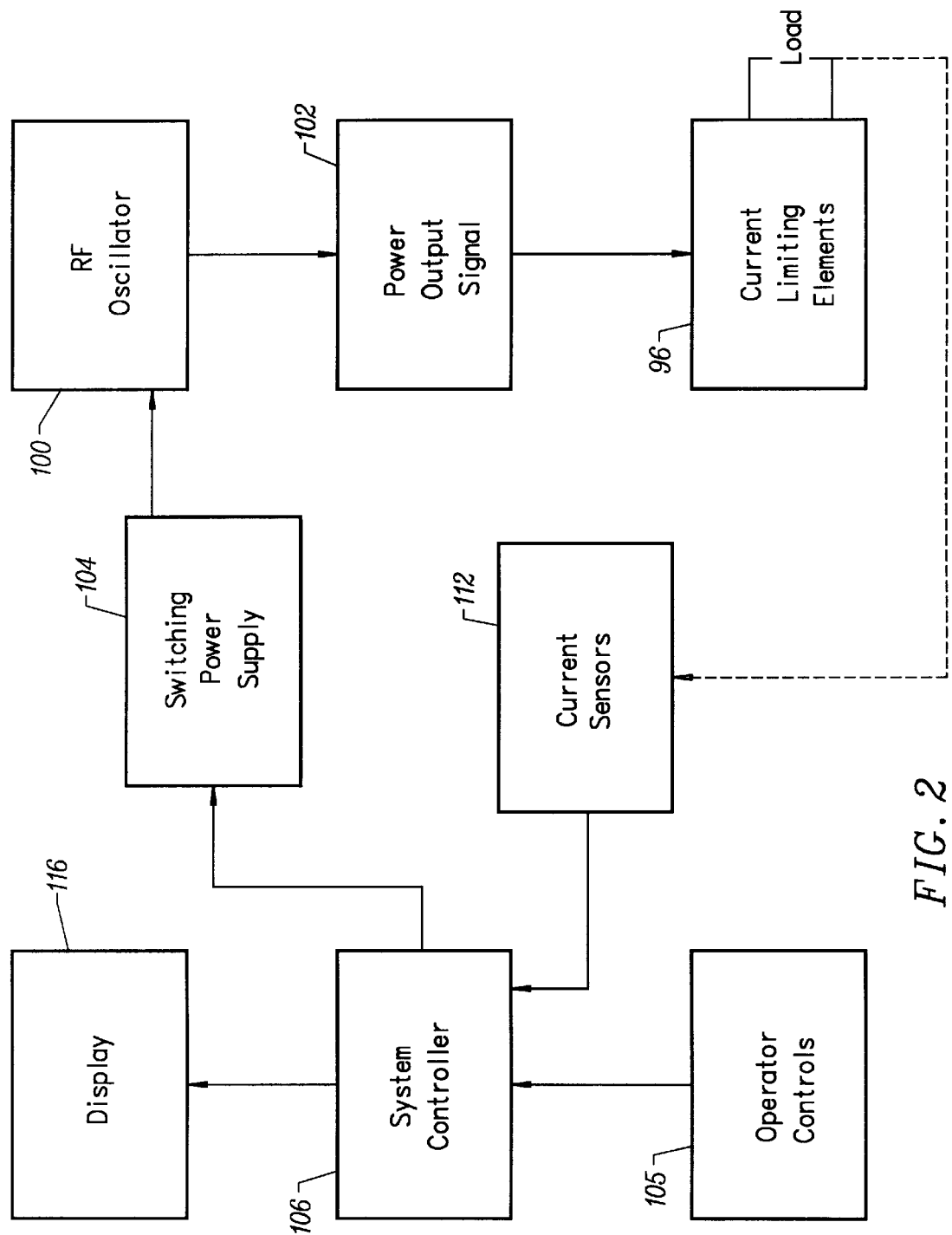
FIG. 2 schematically illustrates one embodiment of a power supply according to the present invention.
Figure 3:
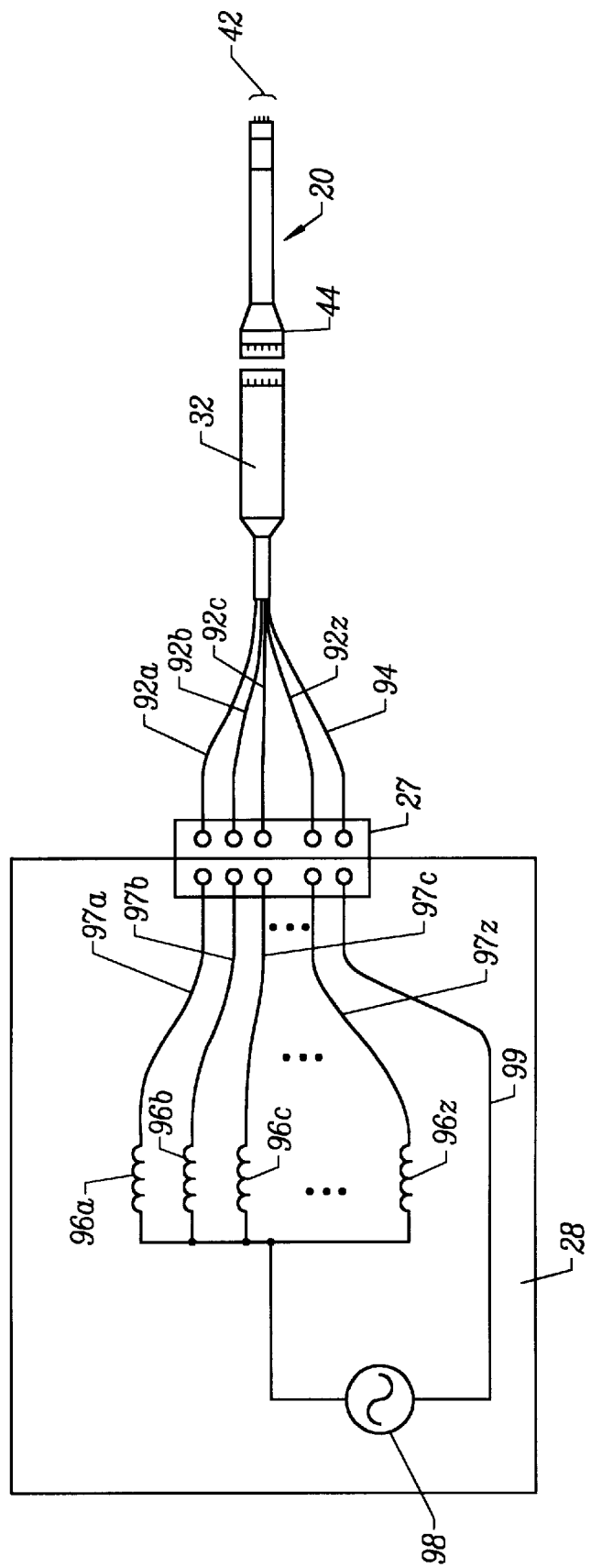
FIG. 3 illustrates an electrosurgical system incorporating a plurality of active electrodes and associated current limiting elements.

Referring now to FIGS. 2 and 3, a representative high frequency power supply for use according to the principles of the present invention will now be described. The high frequency power supply of the present invention is configured to apply a high frequency voltage of about 10 to 500 volts RMS between one or more electrode terminals (and/or coagulation electrode) and one or more return electrodes. In the exemplary embodiment, the power supply applies about 70–350 volts RMS in the ablation mode and about 20 to 90 volts in a subablation mode, preferably 45 to 70 volts in coagulation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular procedure, e.g., arthroscopic surgery, dermatological procedure, ophthalmic procedures, open surgery or other endoscopic surgery procedure.

As shown in FIG. 2, the power supply generally comprises a radio frequency (RF) power oscillator 100 having output connections for coupling via a power output signal 102 to the load impedance, which is represented by the electrode assembly when the electrosurgical probe is in use. In the representative embodiment, the RF oscillator operates at about 100 kHz. The RF oscillator is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 102 is designed to incur minimal voltage decrease (i.e., sag) under load. This improves the applied voltage to the electrode terminals and the return electrode, which improves the rate of volumetric removal (ablation) of tissue.

Power is supplied to the oscillator 100 by a switching power supply 104 coupled between the power line and the RF oscillator rather than a conventional transformer. The switching power supply 140 allows the generator to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 104 operates at about 100 kHz.

A controller 106 coupled to the operator controls 105 (i.e., foot pedals and voltage selector) and display 116, is connected to a control input of the switching power supply 104 for adjusting the generator output power by supply voltage variation. The controller 106 may be a microprocessor or an integrated circuit. The power supply may also include one or more current sensors 112 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the electrode terminals (see FIG. 4).

Alternatively, in one embodiment, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

Figure 4:
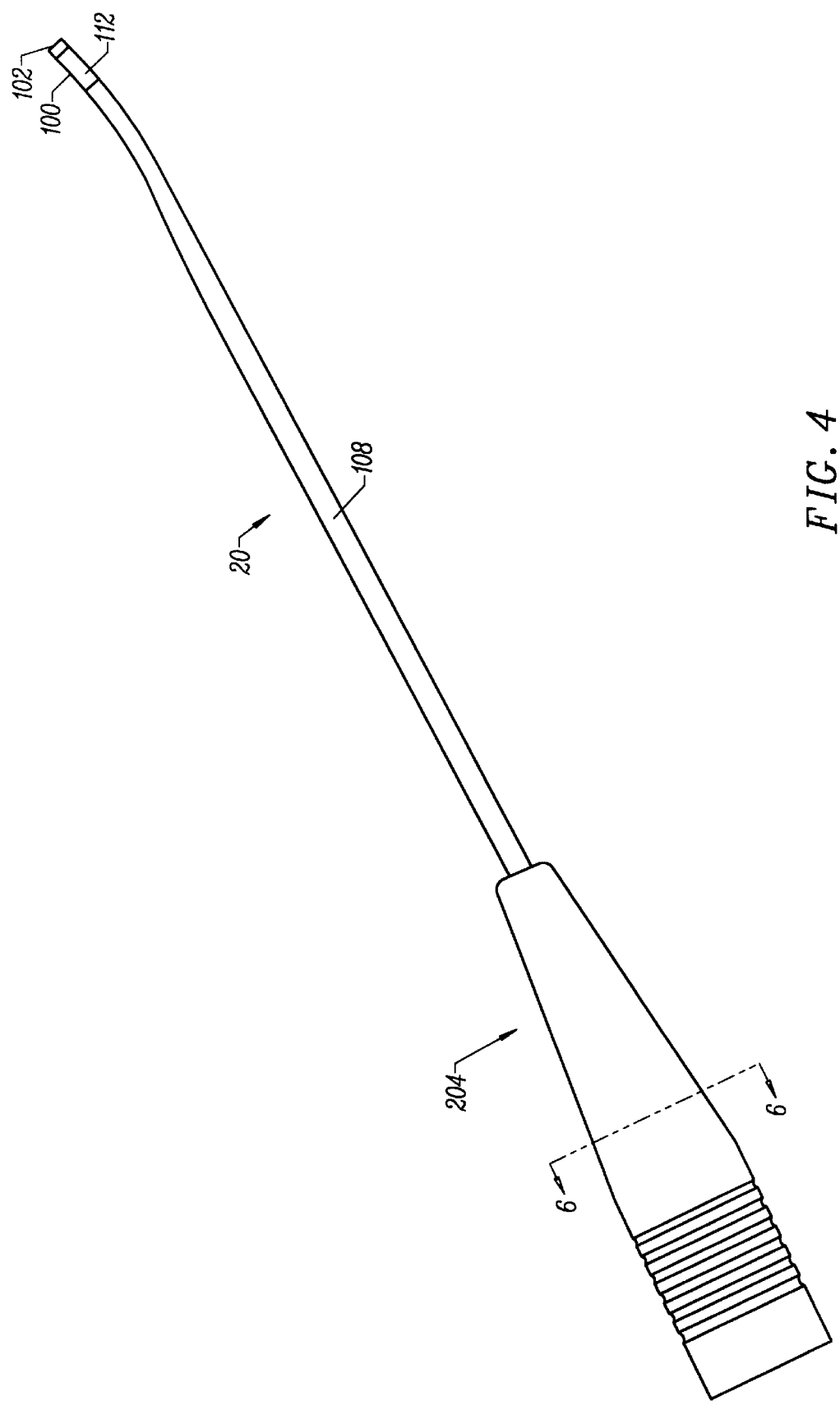
FIG. 4 is a side view of an electrosurgical probe according to the present invention.

Power output signal may also be coupled to a plurality of current limiting elements 96, which are preferably located on the daughter board since the current limiting elements may vary depending on the application. FIG. 4 illustrates an arrangement that may be used in arthroscopic procedures with a multi-electrode probe. As shown, a high frequency power supply 28 comprises a voltage source 98 which is connected to a multiplicity of current limiting elements 96*a*, 96*b*, . . . 96*z*, typically being inductors having an inductance in the range of about 100 to 5000 microhenries, with the particular value depending on the electrode terminal dimensions, the desired ablation rates, and the like. Capacitors having capacitance values in the range of about 200 to 10,000 picofarads may also be used as the current limiting elements. It would also be possible to use resistors as current limiting elements. The current limiting elements any also be part of a resonant circuit structure, as described in detail in PCT/US94/05168, previously incorporated herein by reference.

Figure 5:
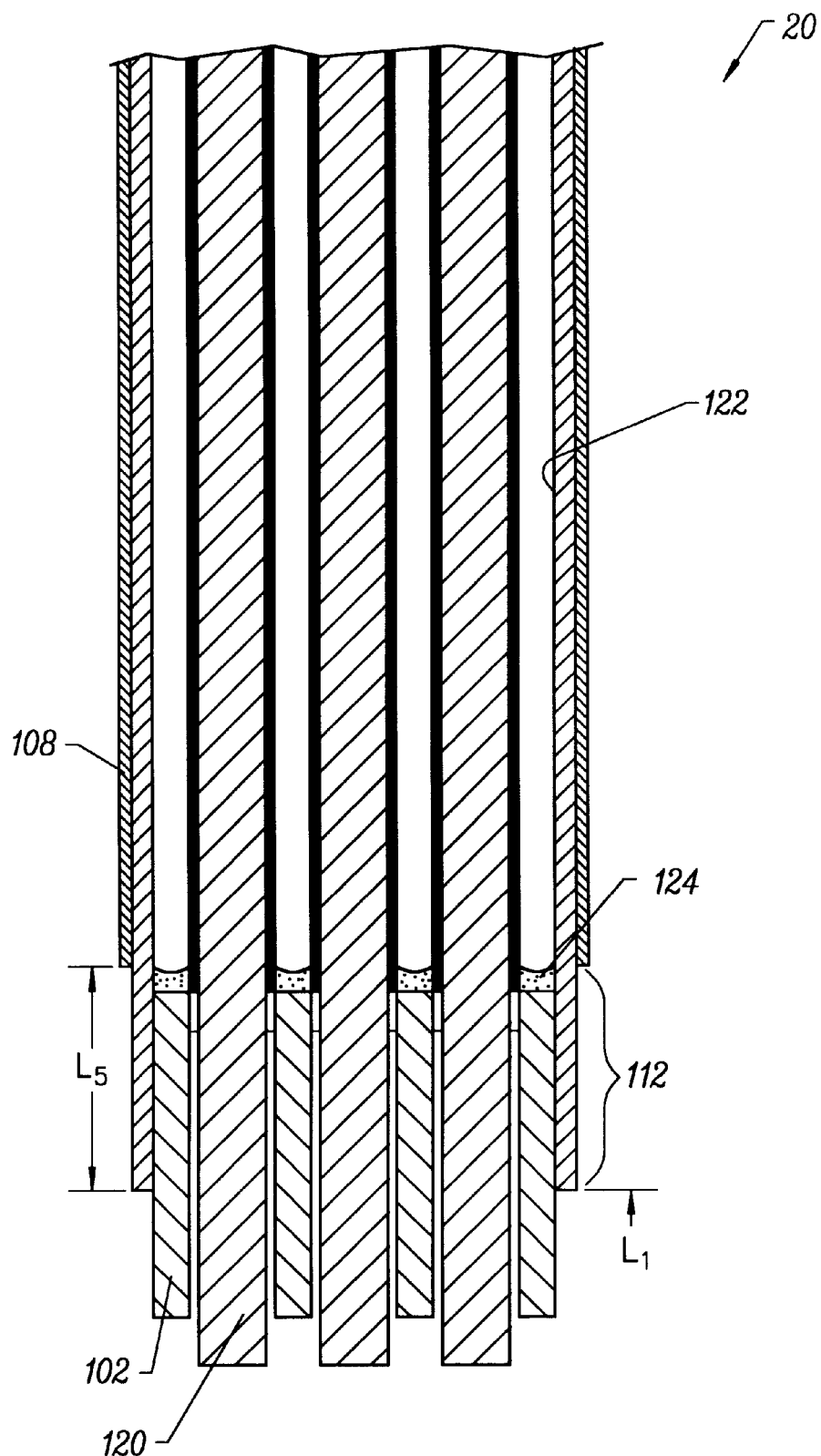
FIG. 5 is an enlarged detailed cross-sectional view of the working end of the electrosurgical probe of FIG. 4.
Figure 6:
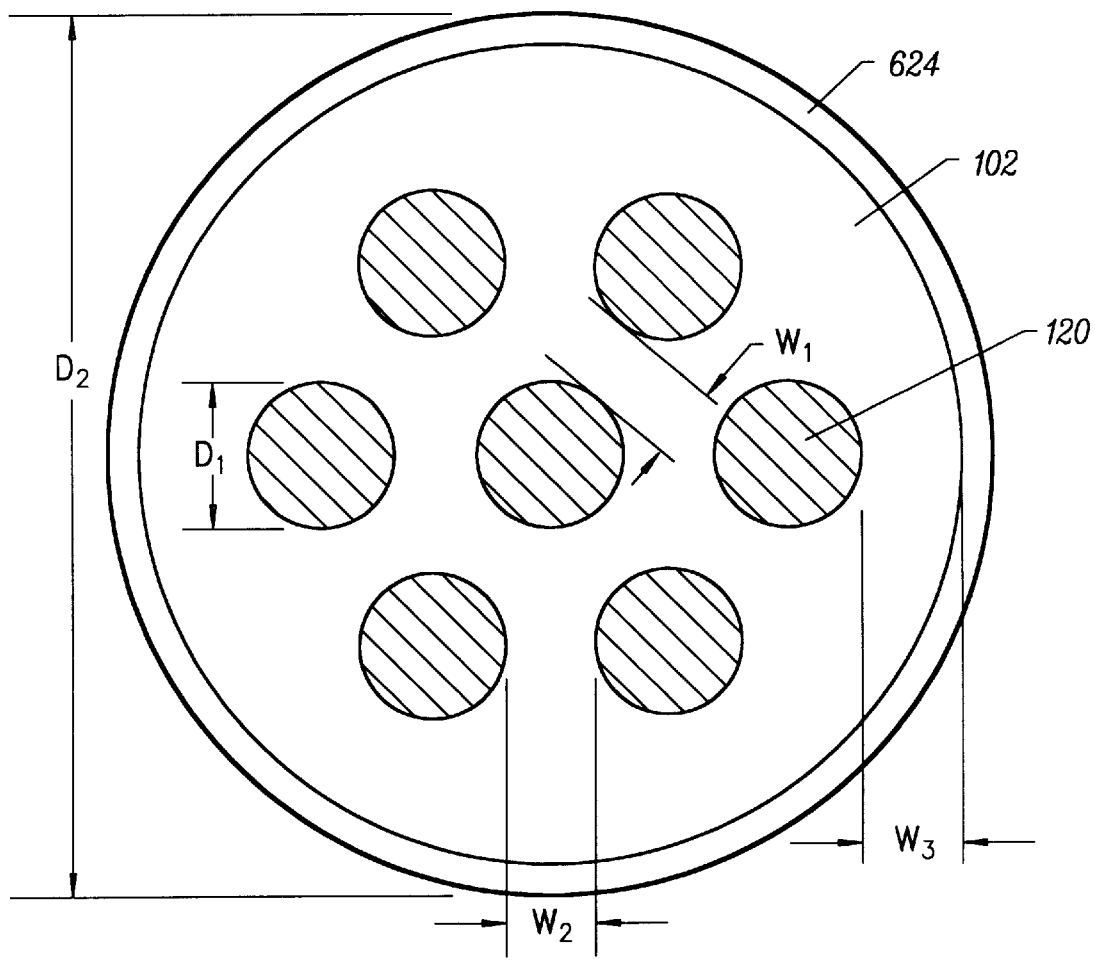
FIG. 6 is a distal end view of the probe of FIG. 4.

FIGS. 4-6 illustrate an exemplary electrosurgical probe 20 constructed according to the principles of the present invention. As shown in FIG. 4, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually a metal, such as tungsten, stainless steel alloys, platinum or its alloys, titanium or its alloys, molybdenum or its alloys, and nickel or its alloys. Shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Figure 7:
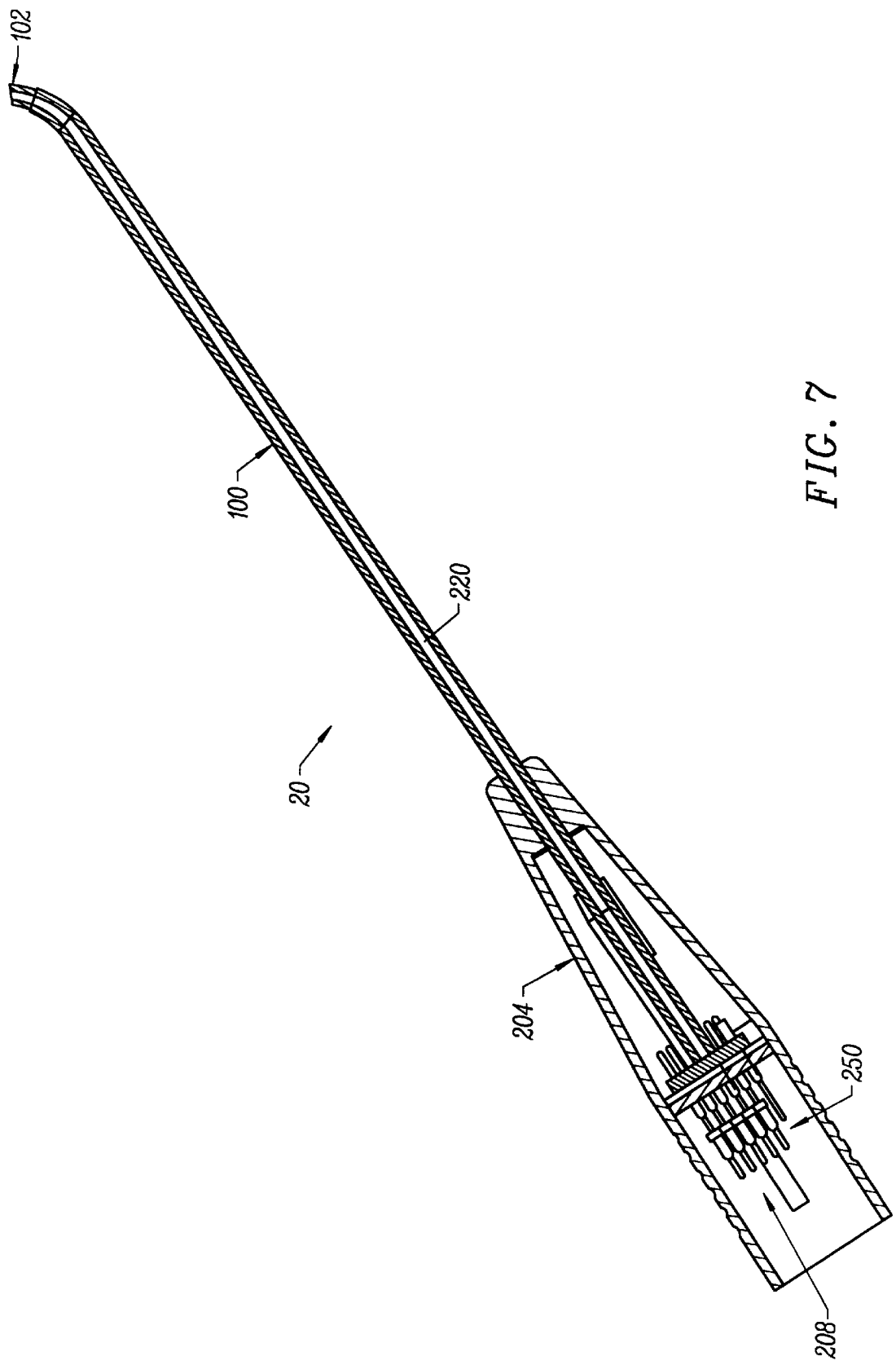
FIGS. 7–10 illustrates an alternative probe according to the present invention, incorporating an aspiration lumen.
Figure 9:
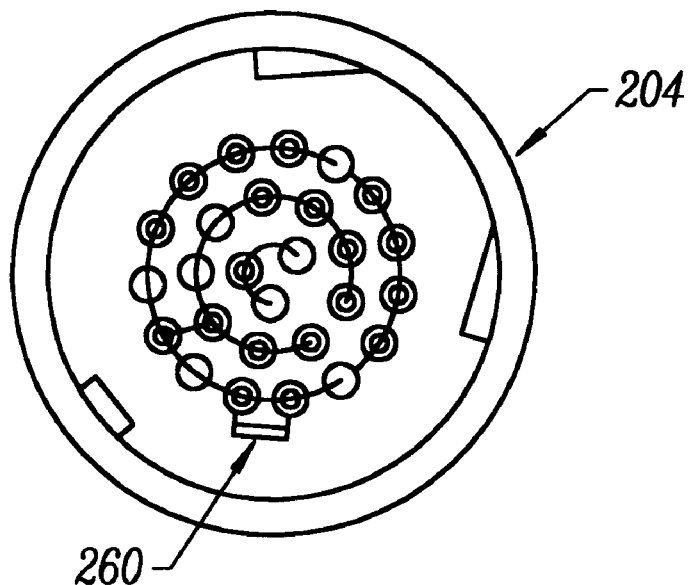

Handle 204 typically comprises a plastic material that is easily molded into a suitable shape for handling by the surgeon. As shown in FIG. 9, handle 204 defines an inner cavity 208 that houses the electrical connections 250 (discussed below), and provides a suitable interface for connection to an electrical connecting cable 22 (see FIG. 1). As shown in FIG. 7, the probe will typically include a coding resistor 260 having a value selected to program different output ranges and modes of operation for the power supply. This allows a single power supply to be used with a variety of different probes in different applications (e.g., dermatology, cardiac surgery, neurosurgery, arthroscopy, etc).

In some embodiments, the probe 20 further includes an identification element that is characteristic of the particular electrode assembly so that the same power supply 28 can be used for different electrosurgical operations. In one embodiment, for example, the probe 20 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the tissue at the target site. The voltage reduction element primarily allows the electrosurgical probe 20 to be compatible with other ArthroCare generators that are adapted to apply higher voltages for ablation or vaporization of tissue. For contraction of tissue, for example, the voltage reduction element will serve to reduce a voltage of about 100 to 135 volts rms (which is a setting of 1 on the ArthroCare Models 970, 980 and 2000 Generators) to about 45 to 60 volts rms, which is a suitable voltage for contraction of tissue without ablation (e.g., molecular dissociation) of the tissue.

Of course, for some procedures, the probe will typically not require a voltage reduction element. Alternatively, the probe may include a voltage increasing element or circuit, if desired.

In the embodiment shown in FIGS. 4–6, an electrode support member 102 extends from the distal end of shaft 100 (usually about 1 to 20 mm), and provides support for a plurality of electrically isolated electrode terminals 120. Electrode support member 102 and electrode terminals 120 are preferably secured to a tubular support member 122 within shaft 100 by adhesive 124. The electrode terminals 120 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 102 is preferably a ceramic, glass or glass/ceramic composition (e.g., aluminum oxide, titanium nitride or the like). Alternatively, electrode support member 620 may include the use of high-temperature biocompatible plastics such as polyether-ether-keytone (PEEK) manufactured by Vitrex International Products, Inc. or polysulfone manufactured by GE Plastics. The adhesive 620 may, by way of example, be an epoxy (e.g., Master Bond EP42HT manufactured by Master Bond) or a silicone-based adhesive.

FIG. 6 illustrates one embodiment of the working end of probe 20. As shown, a total of 7 circular active electrodes or electrode terminals 120 are shown in a symmetrical pattern having an active electrode diameter, D1 in the range from 0.05 mm to 1.5 mm, more preferably in the range from 0.1 mm to 0.75 mm. The interelectrode spacings, W1 and W2 are preferably in the range from 0.1 mm to 1.5 mm and more preferably in the range from 0.2 mm to 0.75 mm. The distance between the outer perimeter of the electrode terminal 120 and the perimeter of the electrode support member, W3 is preferably in the range from 0.1 mm to 1.5 mm and more preferably in the range from 0.2 mm to 0.75 mm. The overall diameter, D2 of the working end of probe 20 is preferably in the range from 0.5 mm to 10 mm and more preferably in the range from 0.5 mm to 5 mm. As discussed above, the shape of the active electrodes may be round, square, triangular, hexagonal, rectangular, tubular, flat strip and the like and may be arranged in a circularly symmetric pattern as shown in FIG. 6 or may, by way of example, be arranged in a rectangular, square, linear pattern, or the like.

In this embodiment, probe 20 includes a tubular cannula 122 extending along shaft 100 radially outward from support member 102 and electrode terminals 120. The material for cannula 122 may be selected from a group of electrically conductive metals so that the cannula 122 functions as both a structural support member for the array of electrode terminals 120 as well as a return electrode 112. The support member 122 is connected to an electrical lead wire (not shown) at its proximal end within a connector housing (not shown) and continues via a suitable connector to power supply 28 to provide electrical continuity between one output pole of high frequency generator 28 and said return electrode 112. The cannula 122 may be selected from the group including stainless steel, copper-based alloys, titanium or its alloys, and nickel-based alloys. The thickness of the cannula 122 is preferably in the range from 0.08 mm to 1.0 mm and more preferably in the range from 0.05 mm to 0.4 mm.

As shown in FIGS. 5 and 6, cannula 122 is covered with an electrically insulating sleeve 108 to protect the patient's body from the electric current. Electrically insulating sleeve 108 may be a coating (e.g., nylon) or heat shrinkable plastic (e.g., fluropolymer or polyester). As shown in FIG. 5, the proximal portion of the cannula 122 is left exposed to function as the return electrode 112. The length of the return electrode 112, L5 is preferably in the range from 1 mm to 30 mm and more preferably in the range from 2 mm to 20 mm. The spacing between the most distal portion of the return electrode 112 and the plane of the tissue treatment surface of the electrode support member 120, L1 is preferably in the range from 0.5 mm to 30 mm and more preferably in the range from 1 mm to 20 mm. The thickness of the electrically insulating sleeve 108 is preferably in the range from 0.01 mm to 0.5 mm and more preferably in the range from 0.02 mm to 0.2 mm.

In the embodiment shown in FIGS. 4–6, the electrically conducting fluid is delivered from a fluid delivery element (not shown) that is separate from probe 20. In arthroscopic surgery, for example, the body cavity will be flooded with isotonic saline and the probe 20 will be introduced into this flooded cavity. Electrically conducting fluid will be continually resupplied to maintain the conduction path between return electrode 112 and electrode terminals 102.

Figure 8:
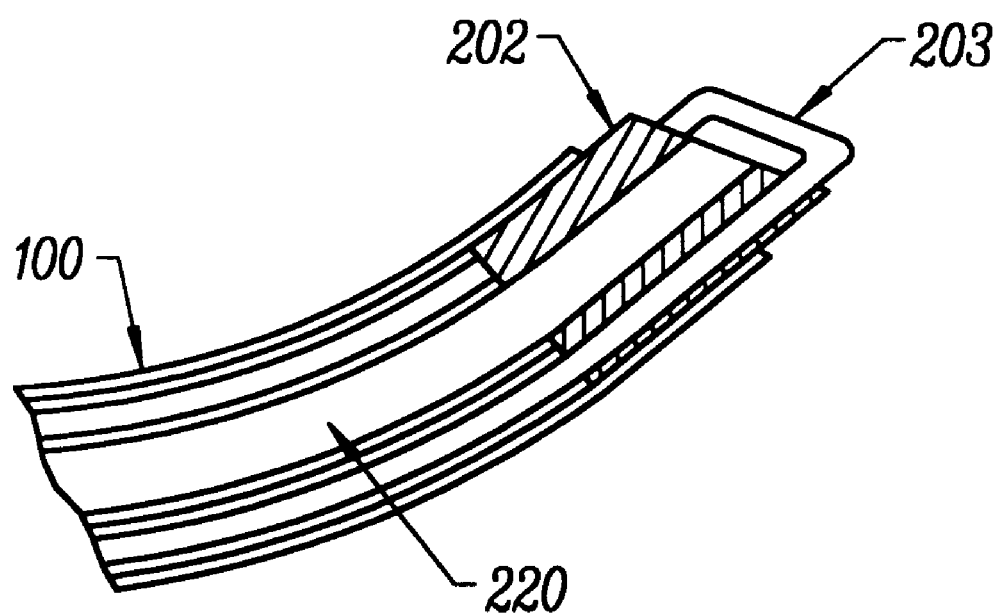

FIGS. 7–10 illustrate another embodiment of the present invention incorporating an aspiration lumen and a loop electrode designed to ablate tissue fragments as they as aspirated into the lumen. As shown in FIG. 7, electrosurgical probe 20 includes an elongated shaft 100 which may be flexible or rigid, a handle 204 coupled to the proximal end of shaft 100 and an electrode support member 102 coupled to the distal end of shaft 100. As shown in FIG. 8, probe 20 includes an active loop electrode 203 and a return electrode 212 spaced proximally from active loop electrode 203. The probe 200 further includes a suction lumen 220 for aspirating excess fluids, bubbles, tissue fragments, and/or products of ablation from the target site. As shown in FIGS. 7 and 8, suction lumen 220 extends through support member 102 to a distal opening 222, and extends through shaft 201 and handle 204 to an external connector 224 for coupling to a vacuum source. Typically, the vacuum source is a standard hospital pump that provides suction pressure to connector 224 and lumen 220.

Figure 20:
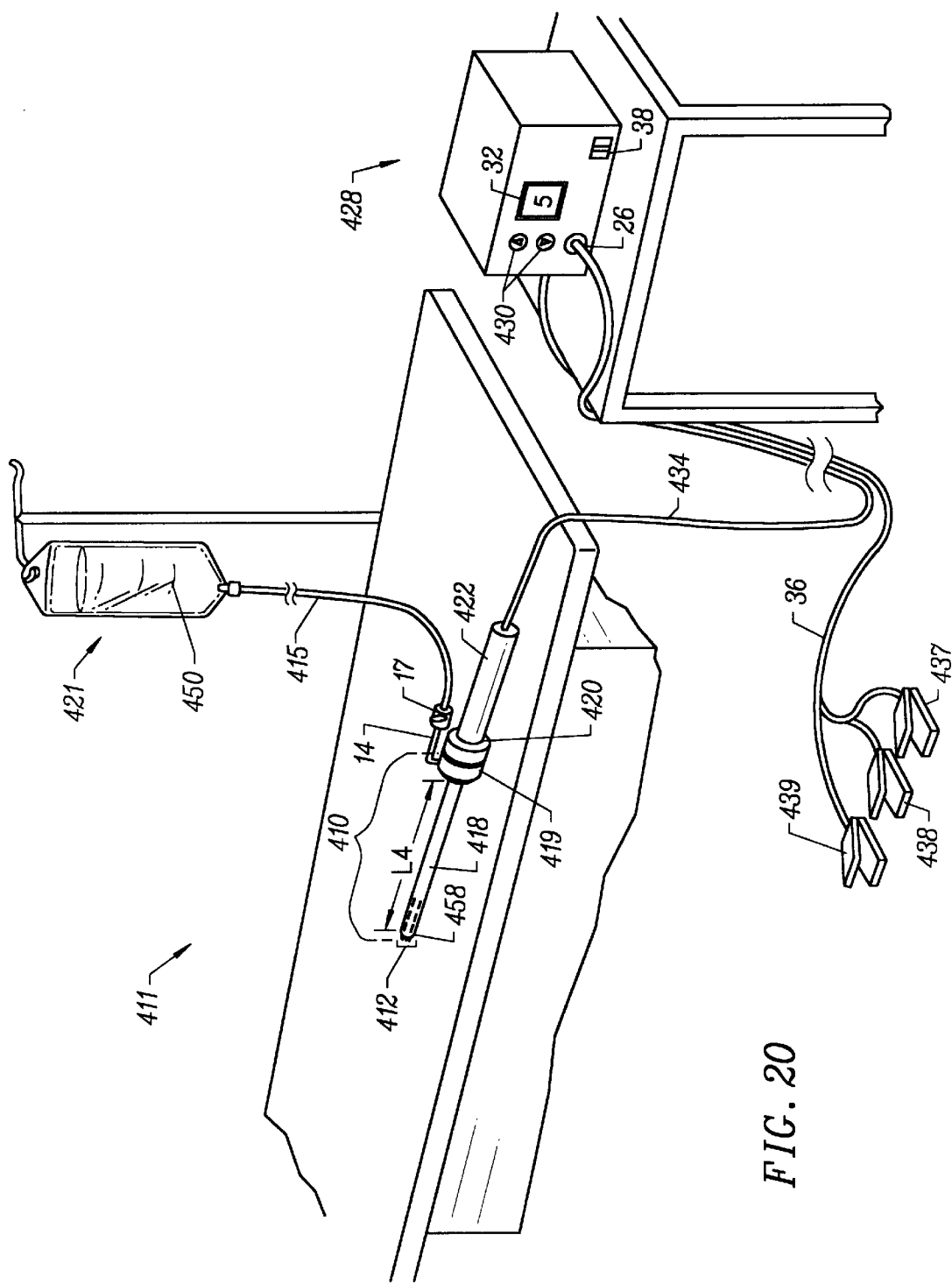
FIG. 20 is a perspective view of another electrosurgical system incorporating a power supply, an electrosurgical probe and a supply of electrically conductive fluid for delivering the fluid to the target site.
Figure 22:
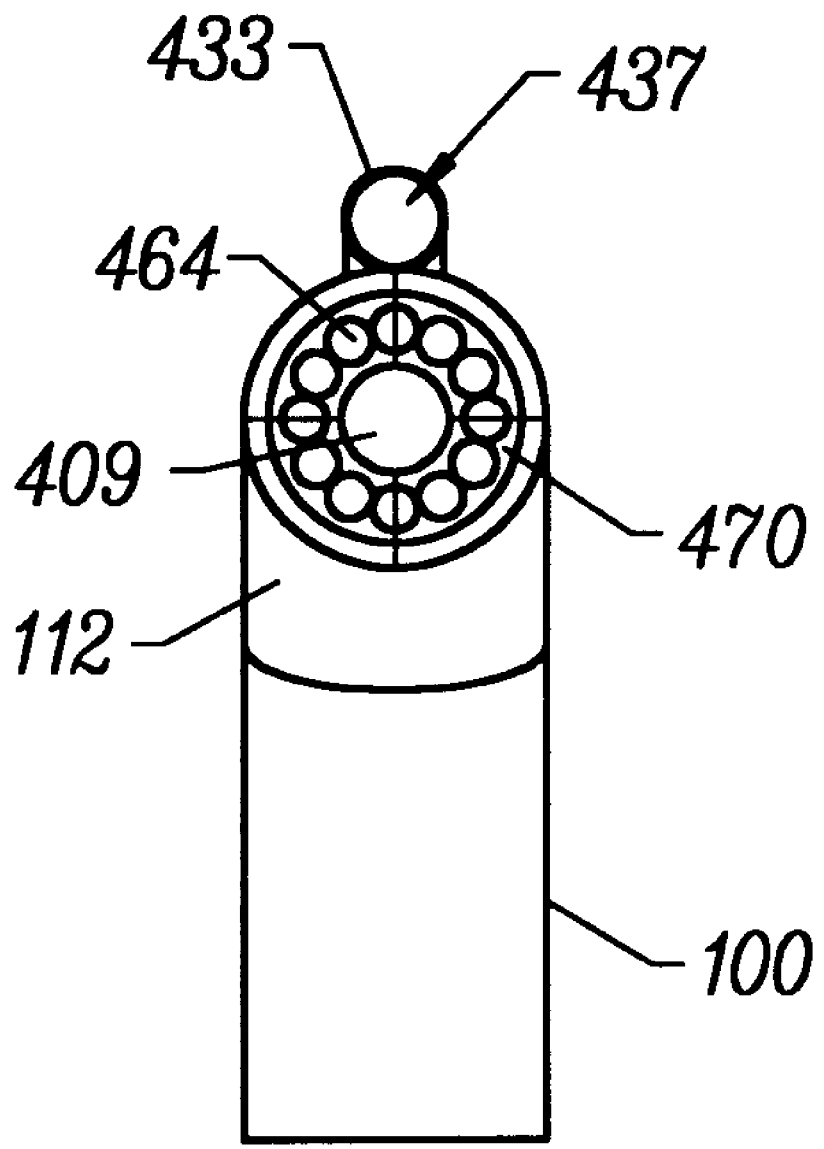
FIG. 22 is a distal end view of the probe of FIG. 21.

Electrode support member 102 extends from the distal end of shaft 201 (usually about 1 to 20 mm), and provides support for loop electrode 203 and a ring electrode 204 (see FIG. 22). As shown in FIG. 20, loop electrode 203 has first and second ends extending from the electrode support member 102. The first and second ends are each coupled to, or integral with, one or more connectors, e.g., wires (not shown), that extend through the shaft of the probe to its proximal end for coupling to the high frequency power supply. The loop electrode usually extends about 0.5 to about 10 mm from the distal end of support member, preferably about 1 to 2 mm. Loop electrode 203 usually extends further away from the support member than the ring electrode 204 to facilitate ablation of tissue. As discussed below, loop electrode 203 is especially configured for tissue ablation, while the ring electrode 204 ablates tissue fragments that are aspirated into suction lumen 220.

Figure 10:
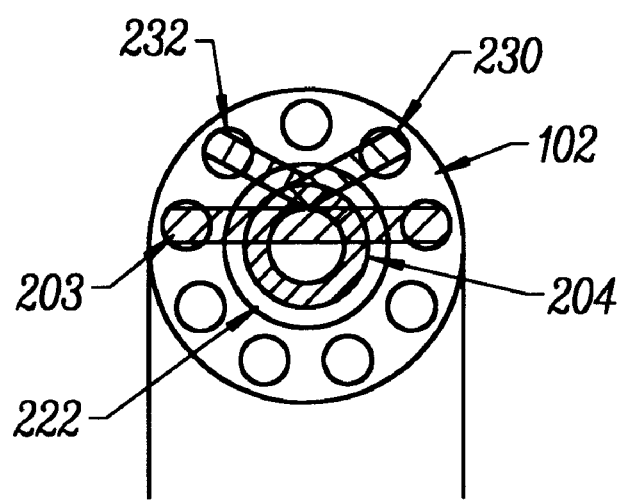
Figure 11:
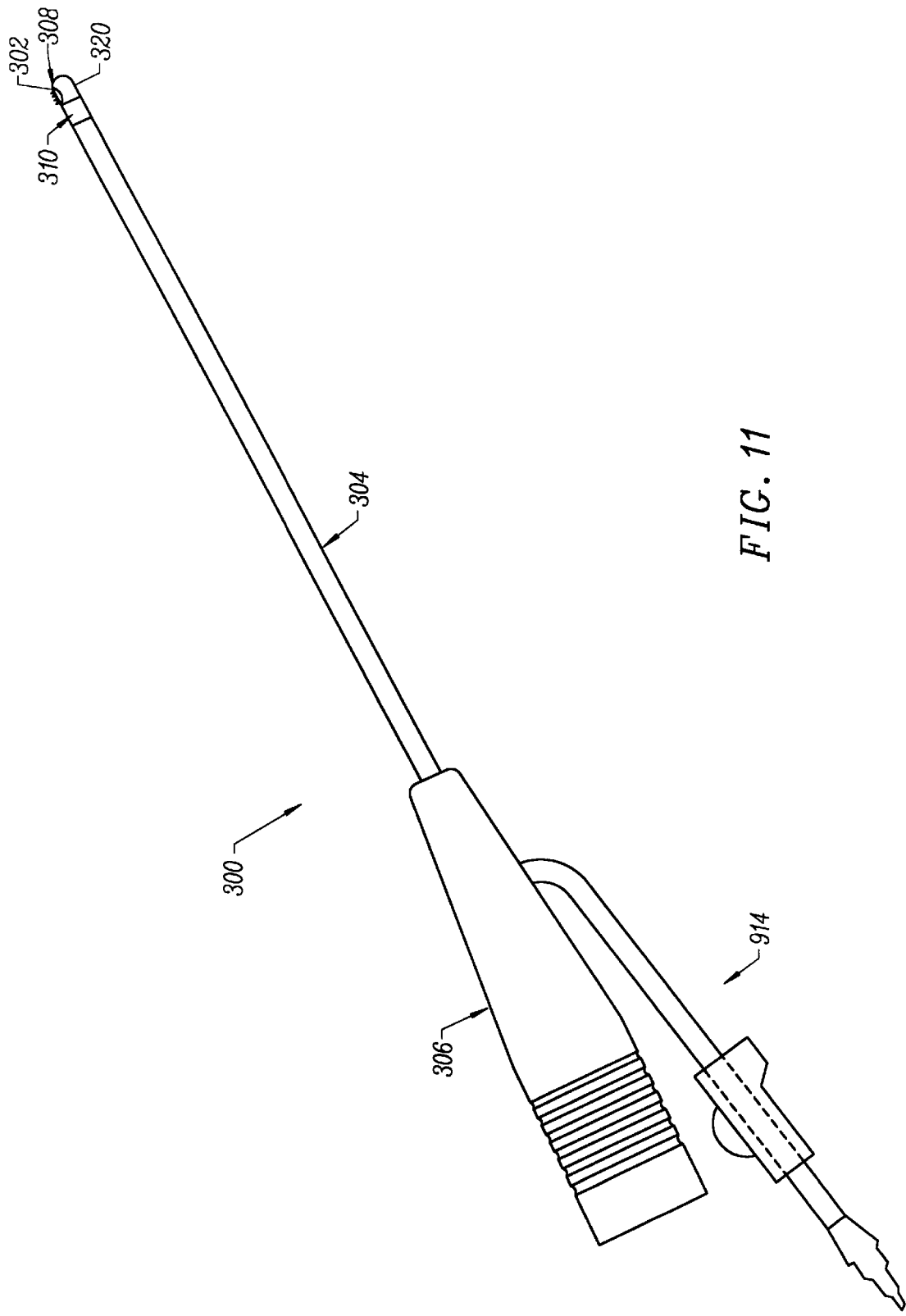
FIG. 11 is a perspective view of yet another embodiment of an electrosurgical probe according to the present invention.

Referring to FIG. 10, ring electrode 204 preferably comprises a tungsten or titanium wire having two ends 230, 232 coupled to electrical connectors (not shown) within support member 102. The wire is bent to form one-half of a figure eight, thereby form a ring positioned over opening 222 of suction lumen 220. This ring inhibits passage of tissue fragments large enough to clog suction lumen 220. Moreover, voltage applied between ring electrode 204 and return electrode 212 provide sufficient energy to ablate these tissue fragments into smaller fragments that are then aspirated through lumen 220. In the presently preferred embodiment, ring electrode 204 and loop electrode 203 are electrically isolated from each other. However, these electrodes 204, 203 may be electrically coupled in some applications.

FIGS. 11–17 illustrate another embodiment of the present invention including an electrosurgical probe 300 incorporating an active screen electrode 302. As shown in FIG. 1, probe 300 includes an elongated shaft 304 which may be flexible or rigid, a handle 306 coupled to the proximal end of shaft 304 and an electrode support member 308 coupled to the distal end of shaft 304. Probe 300 further includes an active screen electrode 302 and a return electrode 310 spaced proximally from active screen electrode 302. In this embodiment, active screen electrode 302 and support member 308 are configured such that the active electrode 302 is positioned on a lateral side of the shaft 304 (e.g., 90 degrees from the shaft axis) to allow the physician to access tissue that is offset from the axis of the portal or arthroscopic opening into the joint cavity in which the shaft 304 passes during the procedure. To accomplish this, probe 300 includes an electrically insulating cap 320 coupled to the distal end of shaft 304 and having a lateral opening 322 for receiving support member 308 and screen electrode 302.

The probe 300 further includes a suction connection tube 314 for coupling to a source of vacuum, and an inner suction lumen 312 (FIG. 12) for aspirating excess fluids, tissue fragments, and/or products of ablation (e.g., bubbles) from the target site. In addition, suction lumen 312 allows the surgeon to draw loose tissue, e.g., synovial tissue, towards the screen electrode 302, as discussed above. Typically, the vacuum source is a standard hospital pump that provides suction pressure to connection tube 314 and lumen 312. However, a pump may also be incorporated into the high frequency power supply.

Figure 12:
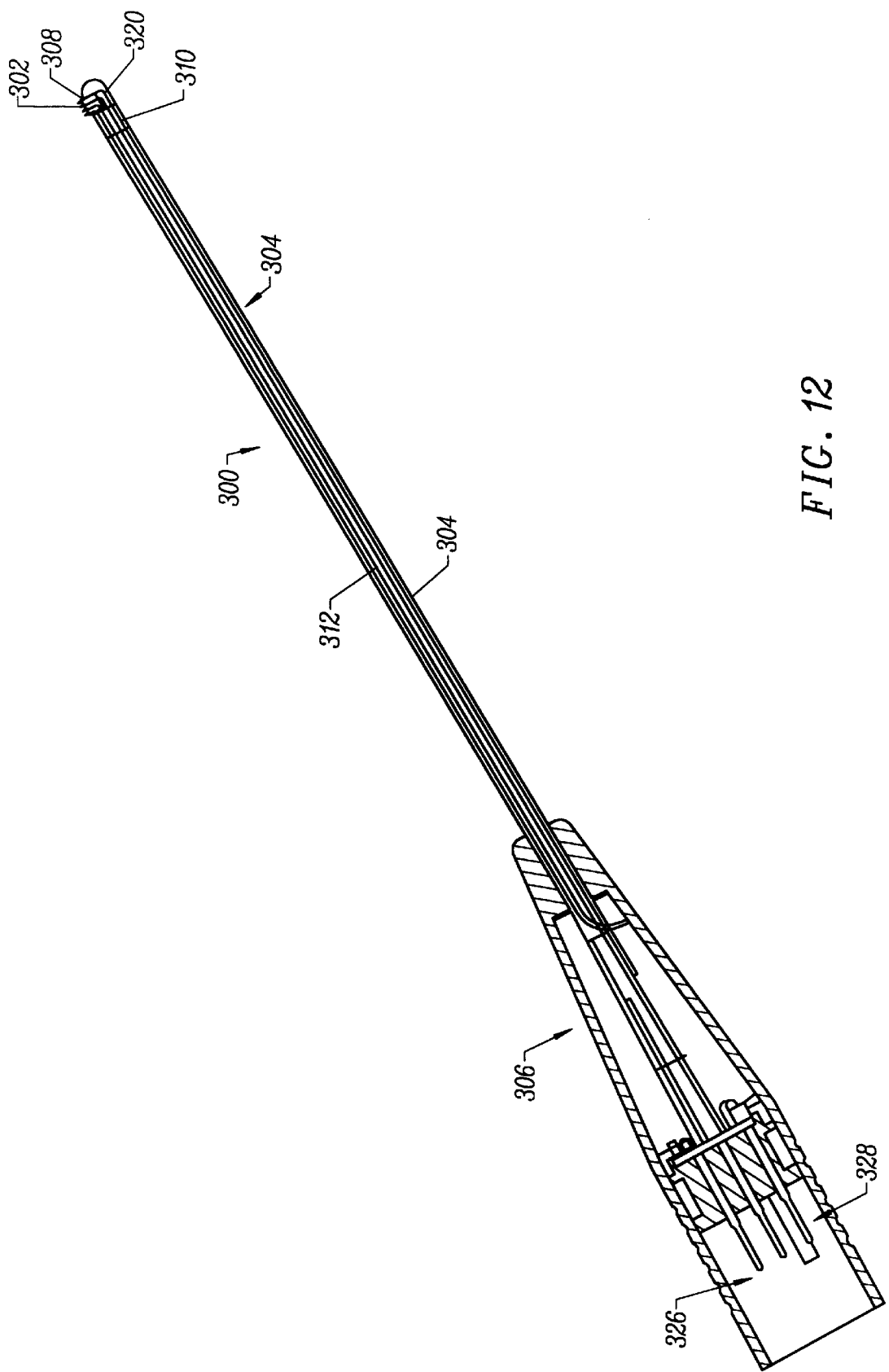
FIG. 12 is a side cross-sectional view of the electrosurgical probe of FIG. 11.
Figure 13:
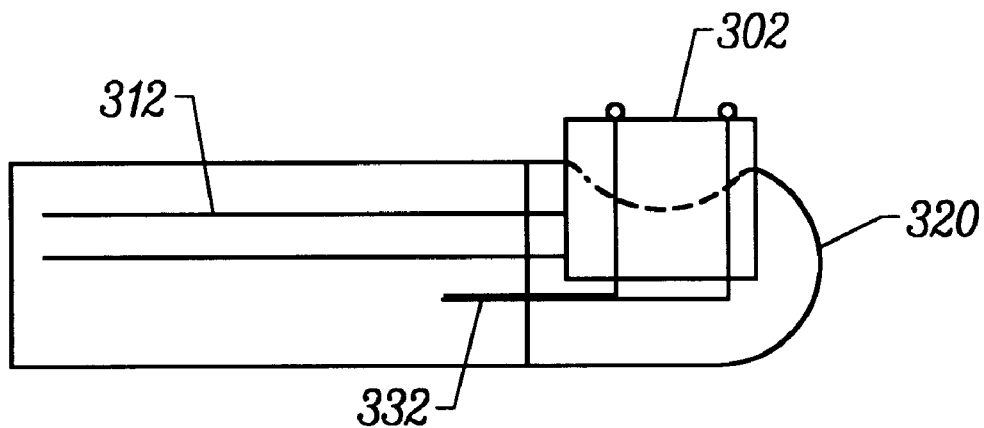
FIG. 13 is an enlarged detailed view of the distal end portion of the probe of FIG. 11.
Figure 14:
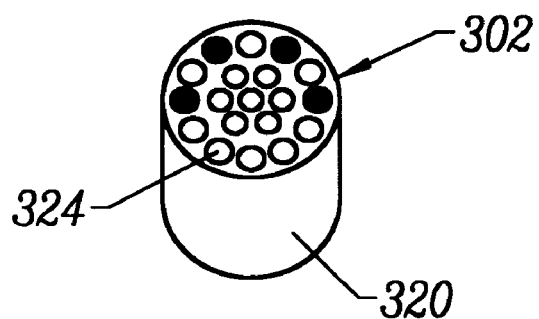
FIGS. 14 and 16 are front and end views, respectively, of the probe of FIG. 11.
Figure 16:
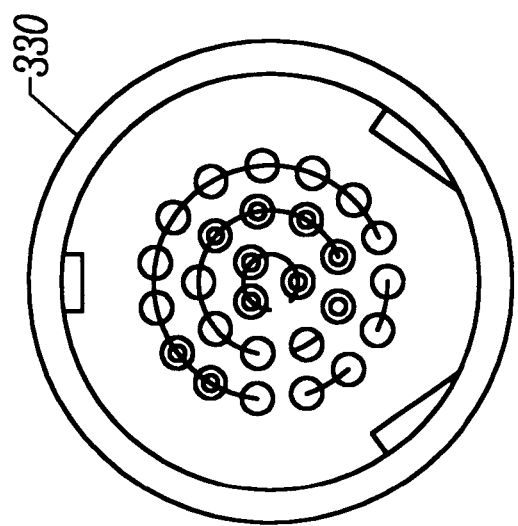

As shown in FIGS. 12, 13 and 16, internal suction lumen 312, which preferably comprises peek tubing, extends from connection tube 314 in handle 306, through shaft 304 to an axial opening 316 in support member 308, through support member 308 to a lateral opening 318. Lateral opening 318 contacts screen electrode 302, which includes a plurality of holes 324 (FIG. 214 for allowing aspiration therethrough, as discussed below.

Figure 15:
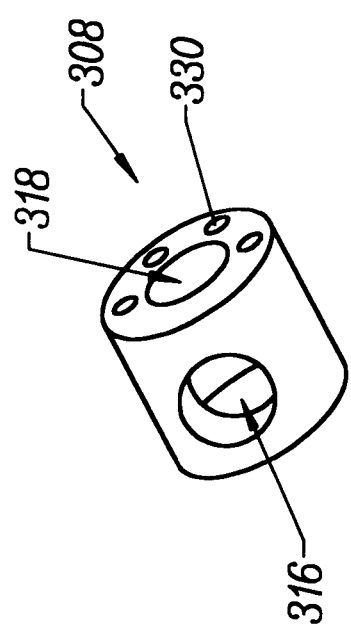
FIG. 15 illustrates a representative insulating support member of the probe of FIG. 11.
Figure 17:
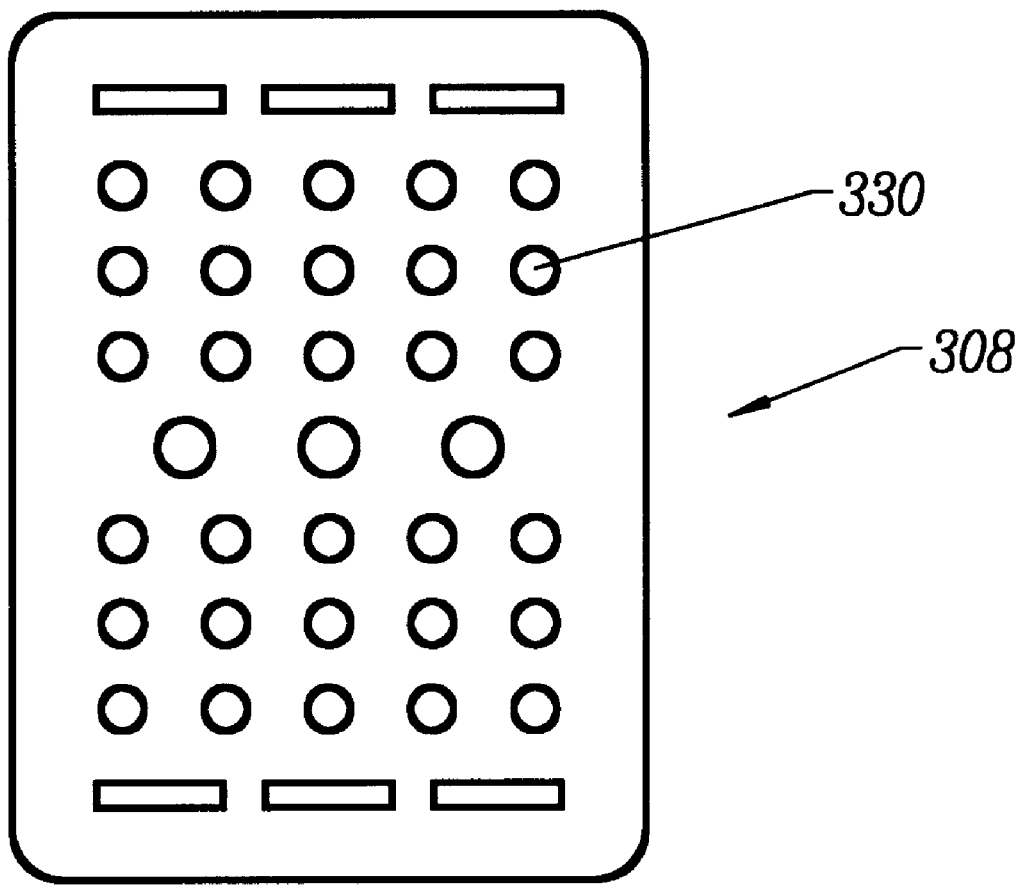
FIG. 17 is an alternative embodiment of the active electrode for the probe of FIG. 11.

As shown in FIG. 12, handle 306 defines an inner cavity 326 that houses the electrical connections 328 (discussed above), and provides a suitable interface for connection to an electrical connecting cable 22 (see FIG. 1). As shown in FIG. 15, the probe will also include a coding resistor 330 having a value selected to program different output ranges and modes of operation for the power supply. This allows a single power supply to be used with a variety of different probes in different applications (e.g., dermatology, cardiac surgery, neurosurgery, arthroscopy, etc).

Referring to FIG. 16, electrode support member 308 preferably comprises an inorganic material, such as glass, ceramic, silicon nitride, alumina or the like, that has been formed with lateral and axial openings 318, 316 for suction, and with one or more smaller holes 330 for receiving electrical connectors 332. In the representative embodiment, support member 308 has a cylindrical shape for supporting a circular screen electrode 302. Of course, screen electrode 302 may have a variety of different shapes, such as the rectangular shape shown in FIG. 17, which may change the associated shape of support member 308. As shown in FIG. 13, electrical connectors 332 extend from connections 328, through shaft 304 and holes 330 in support member 308 to screen electrode 302 to couple the active electrode 302 to a high frequency power supply. In the representative embodiment, screen electrode 302 is mounted to support member 308 by ball wires 334 that extend through holes 336 in screen electrode 302 and holes 330 in support member 308. Ball wires 334 function to electrically couple the screen 302 to connectors 332 and to secure the screen 302 onto the support member 308. Of course, a variety of other methods may be used to accomplish these functions, such as nailhead wires, adhesive and standard wires, a channel in the support member, etc.

The screen electrode 302 will comprise a conductive material, such as tungsten, titanium, molybdenum, stainless steel, aluminum, gold, copper or the like. In some embodiments, it may be advantageous to construct the active and return electrodes of the same material to eliminate the possibility of DC currents being created by dissimilar metal electrodes. Screen electrode 302 will usually have a diameter in the range of about 0.5 to 8 mm, preferably about 1 to 4 mm, and a thickness of about 0.05 to about 2.5 mm, preferably about 0.1 to 1 mm. Electrode 302 will comprise a plurality of holes 324 having sizes that may vary depending on the particular application and the number of holes (usually from one to 50 holes, and preferably about 3 to 20 holes). Holes 324 will typically be large enough to allow ablated tissue fragments to pass through into suction lumen 312, typically being about 2 to 30 mils in diameter, preferably about 5 to 20 mils in diameter. In some applications, it may be desirable to only aspirate fluid and the gaseous products of ablation (e.g., bubbles) so that the holes may be much smaller, e.g., on the order of less than 10 mils, often less than 5 mils.

In the representative embodiment, probe 300 is manufactured as follows: screen electrode 302 is placed on support member 308 so that holes 324 are lined up with holes 330. One or more ball wires 334 are inserted through these holes, and a small amount of adhesive (e.g., epotek) is placed around the outer face of support member 308. The ball wires 334 are then pulled until screen 302 is flush with support member 308, and the entire sub-assembly is cured in an oven or other suitable heating mechanism. The electrode-support member sub-assembly is then inserted through the lateral opening in cap 320 and adhesive is applied to the peek tubing suction lumen 312. The suction lumen 312 is then placed through axial hole 316 in support member 308 and this sub-assembly is cured. The return electrode 310 (which is typically the exposed portion of shaft 304) is then adhered to cap 320.

Figure 18:
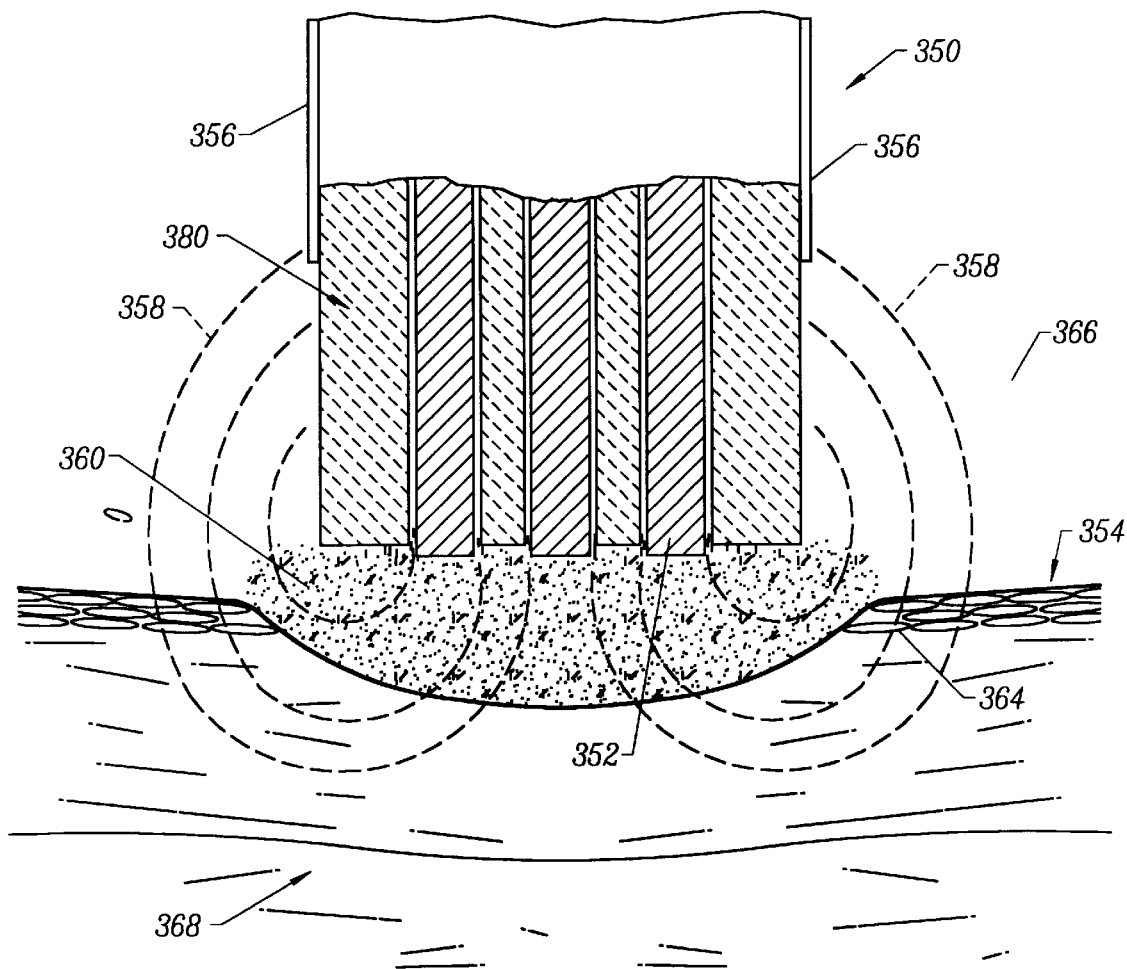
FIG. 18 illustrates a method of ablating tissue with a probe having a plurality of active electrodes according to the present invention.
Figure 19:
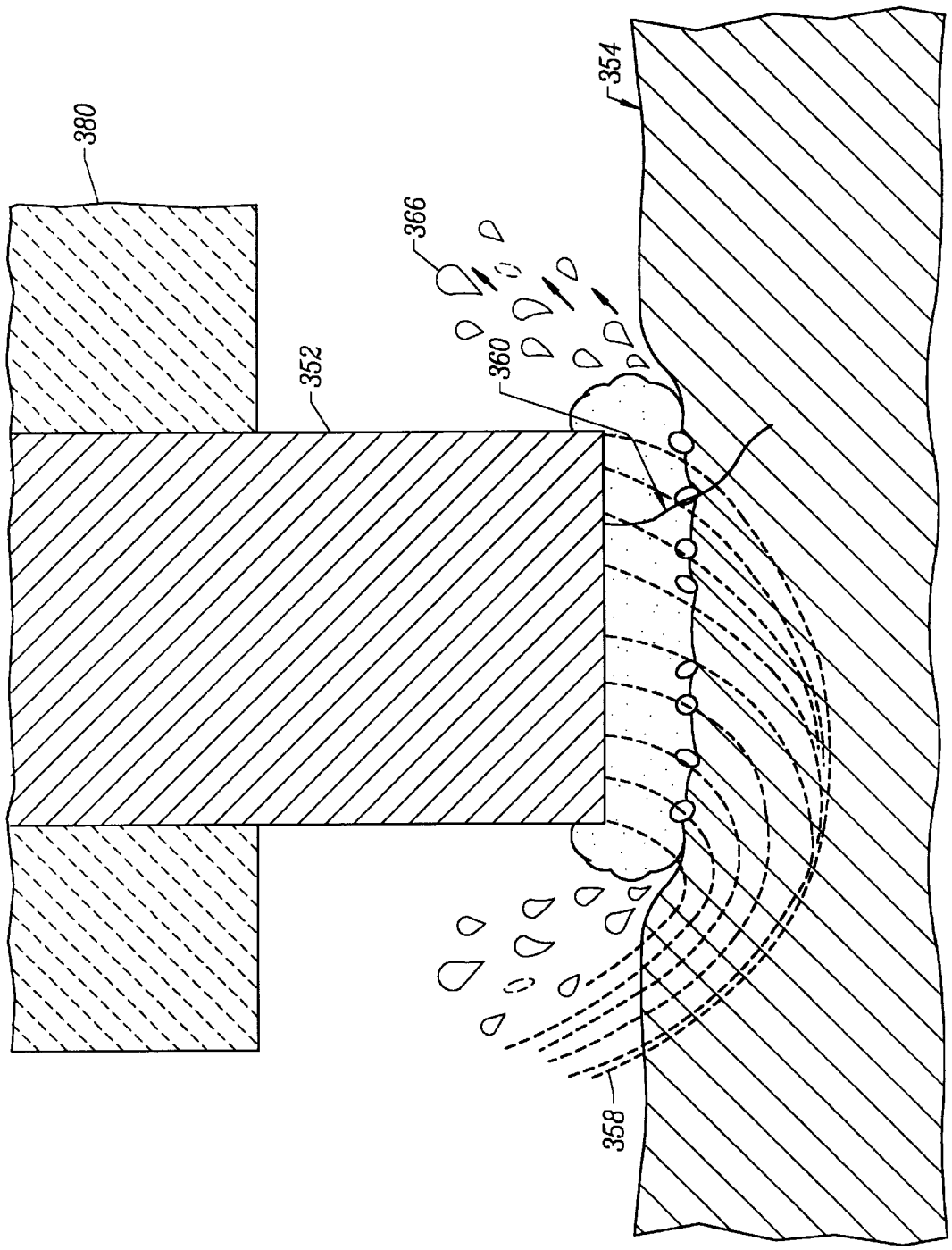
FIG. 19 illustrates a method of ablating tissue with a probe having a single active electrode according to the present invention.

FIGS. 18 and 19 illustrate use of one of the probes 350 of the present invention for ablating tissue. As shown, the distal portion of probe 350 is introduced to the target site (either endoscopically, through an open procedure, or directly onto the patient's skin) and electrode terminal(s) 352 are positioned adjacent tissue (FIG. 19 illustrates a probe having a single active electrode 352, while FIG. 18 illustrates multiple active electrodes 352). In the embodiment, the target site is immersed in electrically conductive fluid, such that the conductive fluid generates a current flow path (see current flux lines 358) between return electrode 356 and the active electrode(s) 352, and the zone between the tissue 354 and electrode support 380 is constantly immersed in the fluid. The power supply (not shown) is then turned on and adjusted such that a high frequency voltage difference is applied between electrode terminal(s) 352 and return electrode 356.

In the representative embodiment, the high frequency voltage is sufficient to convert the electrically conductive fluid between the target tissue 354 and electrode terminal(s) 352 into an ionized vapor layer or plasma 360. As a result of the applied voltage difference between electrode terminal(s) 352 and the target tissue 354 (i.e., the voltage gradient across the plasma layer 360, charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases 366, such as oxygen, nitrogen, carbon dioxide, hydrogen and methane. The short range of the accelerated charged particles within the tissue confines the molecular dissociation process to the surface layer 364 to minimize damage and necrosis to the underlying tissue 368.

Referring now to FIG. 20, an exemplary electrosurgical system 411 for treatment of tissue in 'dry fields' will now be described in detail. Of course, system 411 may also be used in 'wet field', i.e., the target site is immersed in electrically conductive fluid. However, this system is particularly useful in 'dry fields' where the fluid is preferably delivered through electrosurgical probe to the target site. As shown, electrosurgical system 411 generally comprises an electrosurgical handpiece or probe 410 connected to a power supply 428 for providing high frequency voltage to a target site and a fluid source 421 for supplying electrically conducting fluid 450 to probe 410. In addition, electrosurgical system 411 may include an endoscope (not shown) with a fiber optic head light for viewing the surgical site, particularly in sinus procedures or procedures in the ear or the back of the mouth. The endoscope may be integral with probe 410, or it may be part of a separate instrument. The system 411 may also include a vacuum source (not shown) for coupling to a suction lumen or tube 460 (see FIG. 21) in the probe 410 for aspirating the target site.

As shown, probe 410 generally includes a proximal handle 419 and an elongate shaft 418 having an array 412 of electrode terminals 458 at its distal end. A connecting cable 434 has a connector 426 for electrically coupling the electrode terminals 458 to power supply 428. The electrode terminals 458 are electrically isolated from each other and each of the terminals 458 is connected to an active or passive control network within power supply 428 by means of a plurality of individually insulated conductors (not shown). A fluid supply tube 415 is connected to a fluid tube 414 of probe 410 for supplying electrically conducting fluid 450 to the target site.

Figure 21:
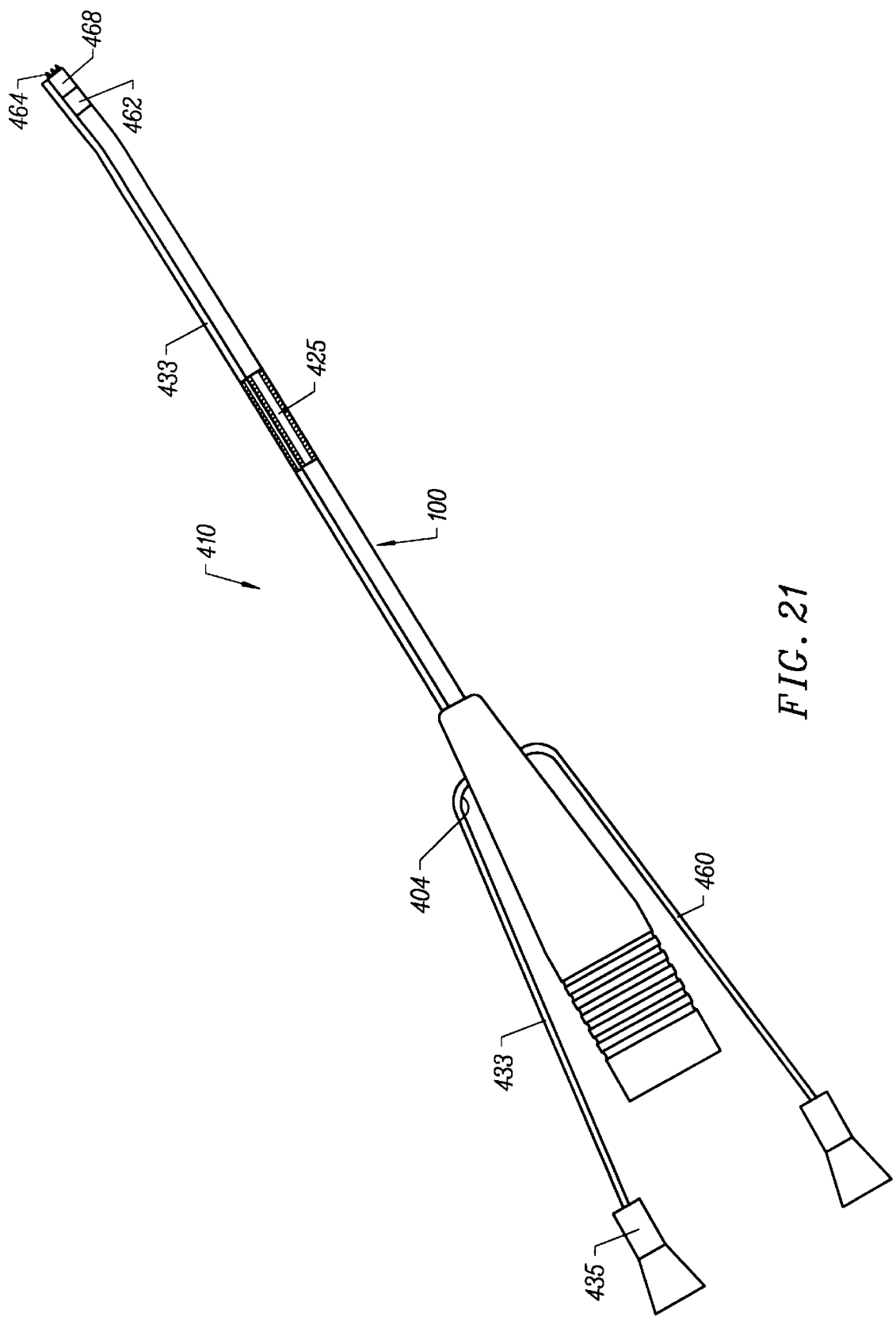
FIG. 21 is a side view of another electrosurgical probe for use with the system of FIG. 20.

FIGS. 21 and 22 illustrate an exemplary embodiment of an electrosurgical probe 410 for use with the system 411 of FIG. 20. As shown, the probe 410 includes a shaft 100, a proximal handle 404, a distal support member 468 and an electrode assembly including a return electrode 462 proximally spaced from one or more electrode terminals 464. Similar to previous embodiments, the return electrode 462 is not directly connected to electrode terminals 464. To complete this current path so that electrode terminals 464 are electrically connected to return electrode 462, electrically conducting fluid (e.g., isotonic saline) is caused to flow therebetween. In the representative embodiment, probe 410 includes a fluid connector 435 for coupling a fluid tube 433 to a source of electrically conductive fluid, such as a pump or a gravity driven fluid source. The electrically conducting fluid is delivered through fluid tube 433 to opening 437, as described above. Electrically conducting fluid will be continually resupplied to maintain the conduction path between return electrode 462 and electrode terminals 464.

In the representative embodiment, fluid tube 433 comprises peek tubing or a similar type of tubing material. In alternative embodiments, the fluid path may be formed in probe 410 by, for example, an inner lumen or an annular gap between the return electrode 462 and a tubular support member within shaft 100 (see FIG. 22). This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or suitable pumping device), is coupled to probe 410 via a fluid supply tube (not shown) that may or may not have a controllable valve.

Referring to FIG. 22, the electrically isolated electrode terminals 464 are spaced apart over tissue treatment surface 470 of electrode support member 468. The tissue treatment surface and individual electrode terminals 464 will usually have dimensions within the ranges set forth above. In the representative embodiment, the tissue treatment surface 470 has a circular cross-sectional shape with a diameter in the range of about 1 to 20 mm. The individual electrode terminals 464 preferably extend outward from tissue treatment surface 474 by a distance of about 0.0 to 4 mm, usually about 0.2 to 2 mm. Applicant has found that this configuration increases the high electric field intensities and associated current densities around electrode terminals 464 to facilitate the ablation of tissue as described in detail above. Of course, in other embodiments, the electrode terminals 464 may be flush with tissue treatment surface 474, be recessed from treatment surface 474, or extend further outward than 2 mm, depending on the desired treatment outcome.

In the embodiment of FIG. 22, the probe includes a single, larger opening 409 in the center of tissue treatment surface 470, and a plurality of electrode terminals (e.g., about 3 to 15 electrode terminals) around the perimeter of surface 470. Alternatively, the probe may include a single, annular, or partially annular, electrode terminal at the perimeter of the tissue treatment surface. The central opening 409 is coupled to a suction lumen 425 within shaft 100 and a suction tube 461 (FIG. 21) for aspirating tissue, fluids, and/or gases from the target site. In this embodiment, the electrically conductive fluid generally flows radially inward past electrode terminals 464 and then back through the opening 209. Aspirating the electrically conductive fluid during surgery allows the surgeon to see the target site, and it prevents the dispersal of gases, bone tissue fragments and/or calcified deposits into the patient's body.

In some embodiments, the probe 410 will also include one or more aspiration electrode(s) (not shown) coupled to the aspiration lumen 425 for inhibiting clogging during aspiration of tissue fragments from the surgical site. A more complete description of these embodiments can be found in commonly assigned co-pending application Ser. No. 09/010, 382, filed Jan. 21, 1998 (Attorney Docket No. A-6), the complete disclosure of which is incorporated herein by reference for all purposes.

Figure 23:
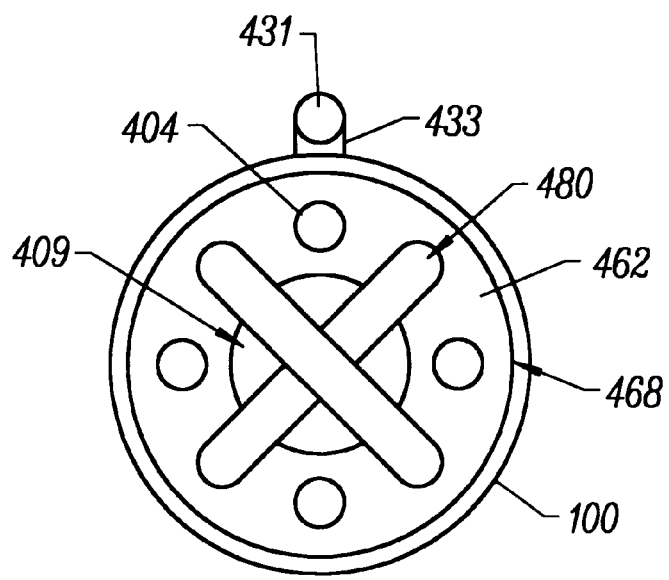
FIGS. 23–26 are distal end view of alternative probes according to the present invention.
Figure 24:
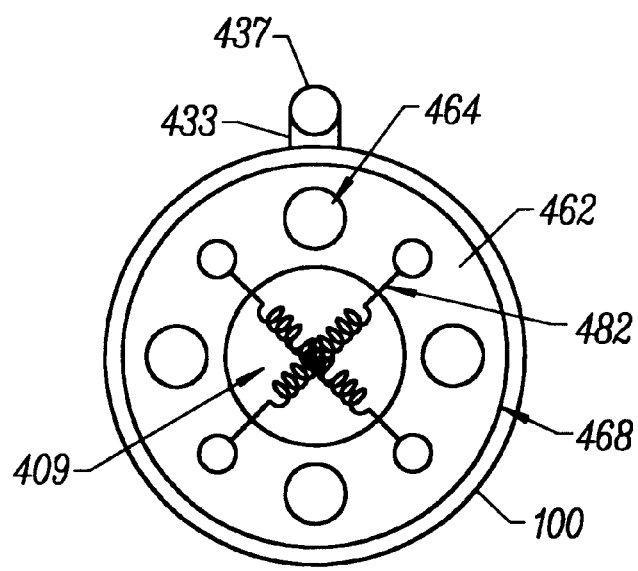
Figure 25:
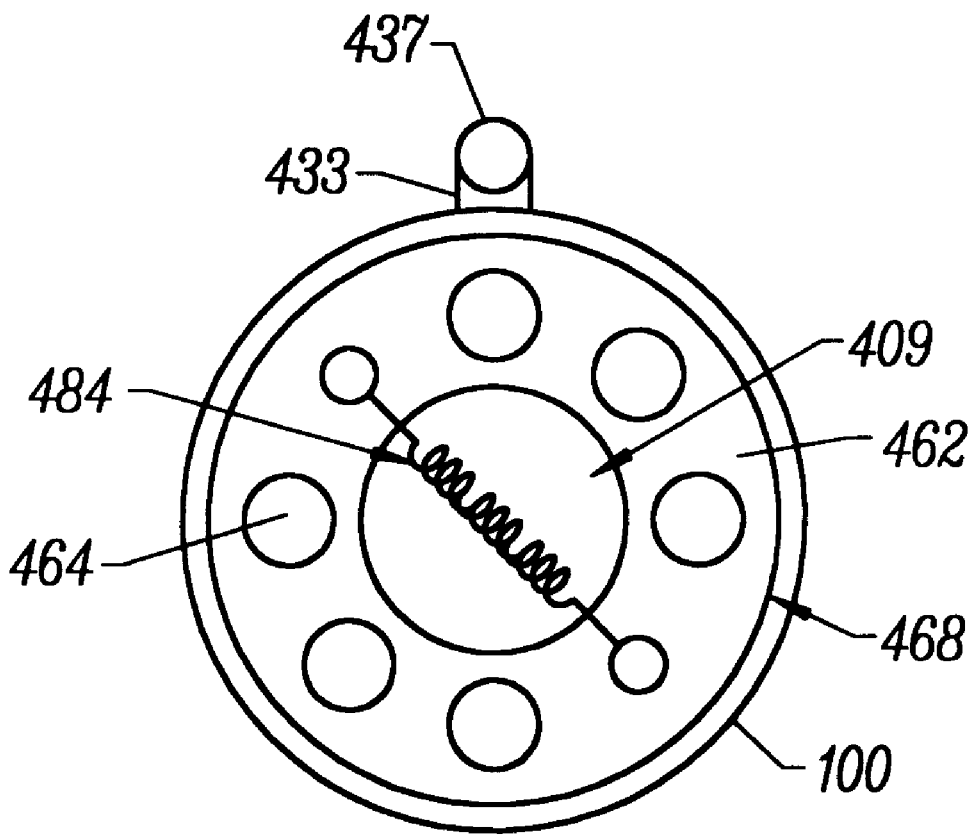
Figure 26:
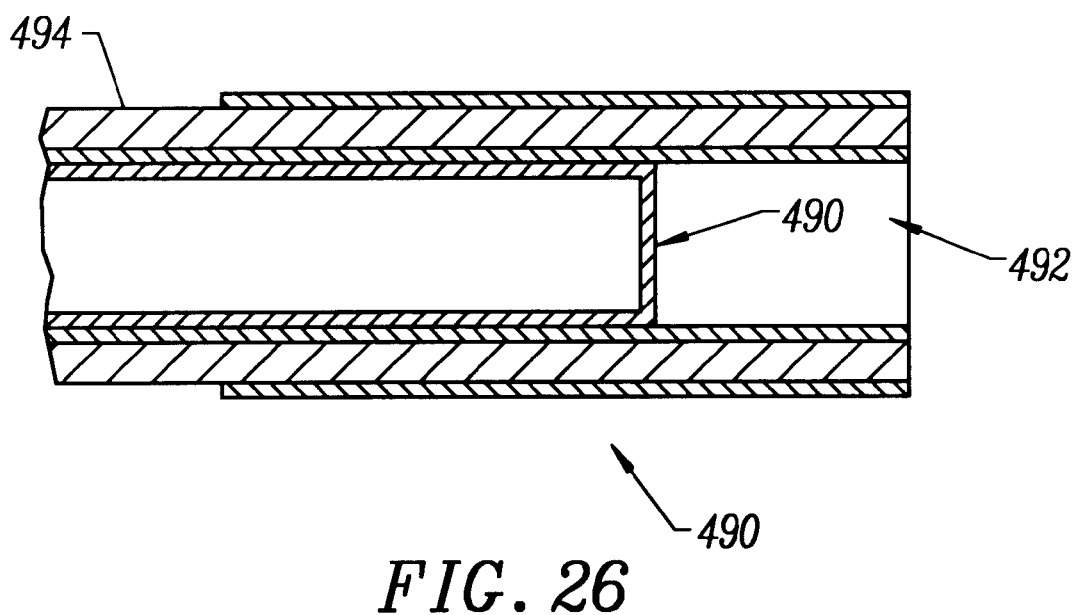

FIGS. 23–26 illustrate alternative embodiments of the probe 410, each one incorporating one or more aspiration electrodes positioned in front of opening 409 of aspiration lumen 425. As shown in FIG. 23, two of the electrode terminals 464 comprise loop electrode 480 that cross over the distal opening 609. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 24 and 25. Alternatively, the electrodes may be formed within suction lumen proximal to the distal opening 409, as shown in FIG. 26. The main function of loop electrodes 480 is to ablate portions of tissue that are drawn into the suction lumen to prevent clogging of the lumen.

Loop electrodes 4800 are electrically isolated from the other electrode terminals 464, which can be referred to hereinafter as the ablation electrodes 464. Loop electrodes 480 may or may not be electrically isolated from each other. Loop electrodes 480 will usually extend only about 0.05 to 4 mm, preferably about 0.1 to 1 mm from the tissue treatment surface of electrode support member 464. In one embodiment, loop electrodes 480 are electrically isolated from the other electrode terminals 464, and they must be separately activated at the power supply 28. In other embodiments, loop electrodes 480 will be activated at the same time that electrode terminals 464 are activated. In this case, applicant has found that the plasma layer typically forms when tissue is drawn adjacent to loop electrodes 480.

Referring now to FIGS. 24 and 25, alternative embodiments for aspiration electrodes will now be described. As shown in FIG. 24, the aspiration electrodes may comprise a pair of coiled electrodes 482 that extend across distal opening 409 of the suction lumen. The larger surface area of the coiled electrodes 482 usually increases the effectiveness of the electrodes 482 on tissue fragments passing through opening 409. In FIG. 25, the aspiration electrode comprises a single coiled electrode 484 passing across the distal opening 409 of suction lumen. This single electrode 484 may be sufficient to inhibit clogging of the suction lumen. Alternatively, the aspiration electrodes may be positioned within the suction lumen proximal to the distal opening 609. Preferably, these electrodes are close to opening 409 so that tissue does not clog the opening 609 before it reaches electrodes 484. In this embodiment, a separate return electrode (not shown) may be provided within the suction lumen to confine the electric currents therein.

Referring to FIG. 26, another embodiment of the present invention incorporates an aspiration electrode 490 within the aspiration lumen 492 of the probe. As shown, the electrode 490 is positioned just proximal of distal opening 409 so that the tissue fragments are ablated as they enter lumen 492. In the representation embodiment, the aspiration electrode 490 comprises a loop electrode that stretches across the aspiration lumen 492. However, it will be recognized that many other configurations are possible. In this embodiment, the return electrode 494 is located outside of the probe as in the previously embodiments. Alternatively, the return electrode(s) may be located within the aspiration lumen 492 with the aspiration electrode 490. For example, the inner insulating coating 493 may be exposed at portions within the lumen 492 to provide a conductive path between this exposed portion of return electrode 494 and the aspiration electrode 490. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 492 along with the tissue fragments.

In use with the present invention, gases will be aspirated through opening 409 and suction tube 460 (FIG. 21) to a vacuum source. In addition, excess electrically conductive fluid, and other fluids (e.g., blood) will be aspirated from the target site to facilitate the surgeon's view. Applicant has also found that tissue fragments are also aspirated through opening 409 into suction lumen and tube 460 during the procedure. These tissue fragments are ablated or dissociated with loop electrodes 480 (FIG. 23) with a similar mechanism described above. Namely, as electrically conductive fluid and tissue fragments are aspirated into loop electrodes 480, these electrodes are activated so that high frequency voltage is applied to loop electrodes 480 and return electrode 462 (of course, the probe may include a different, separate return electrode for this purpose). The voltage is sufficient to vaporize the fluid, and create a plasma layer between loop electrodes 480 and the tissue fragments so that portions of the tissue fragments are ablated or removed. This reduces the volume of the tissue fragments as they pass through suction lumen to minimize clogging of the lumen.

In addition, the present invention is particularly useful for removing elastic tissue, such as the synovial tissue found in joints. In arthroscopic procedures, this elastic synovial tissue tends to move away from instruments within the conductive fluid, making it difficult for conventional instruments to remove this tissue. With the present invention, the probe is moved adjacent the target synovial tissue, and the vacuum source is activated to draw the synovial tissue towards the distal end of the probe. The aspiration and/or active electrode terminals are then energized to ablate this tissue. This allows the surgeon to quickly and precisely ablate elastic tissue with minimal thermal damage to the treatment site.

Figure 27A:
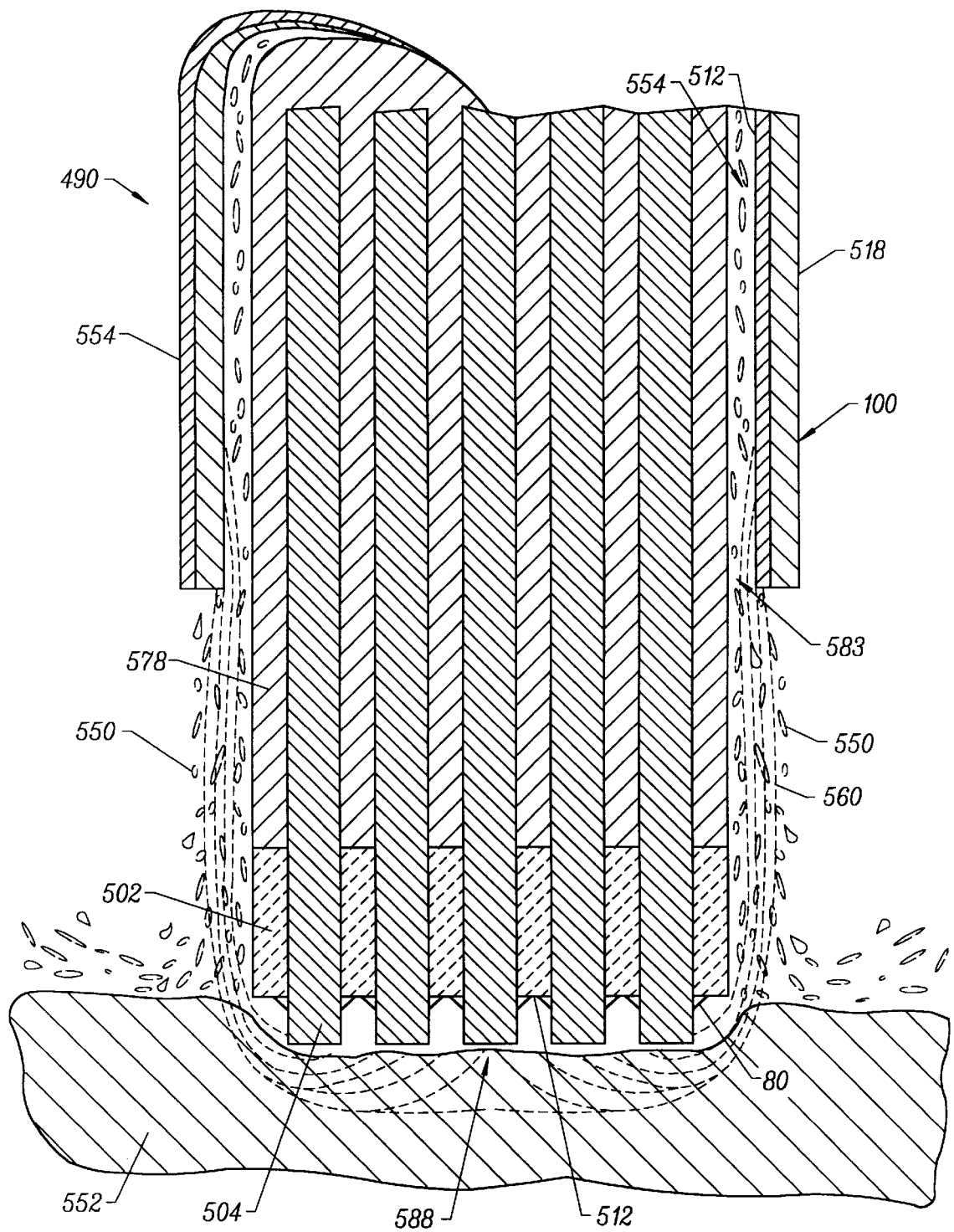
FIGS. 27A–27C are cross-sectional views of the distal portions of three different embodiments of an electrosurgical probe according to the present invention.
Figure 27B:
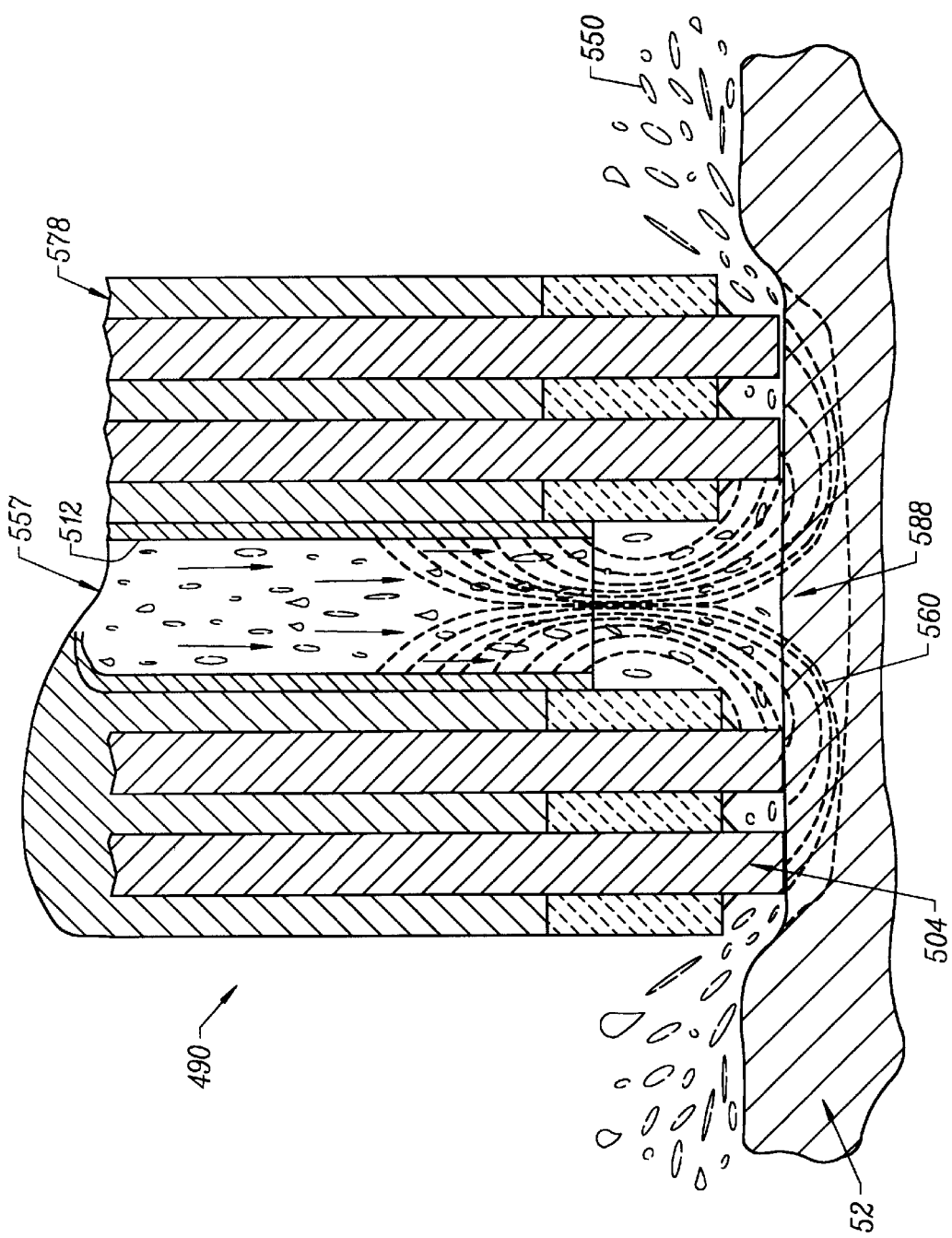
Figure 27C:
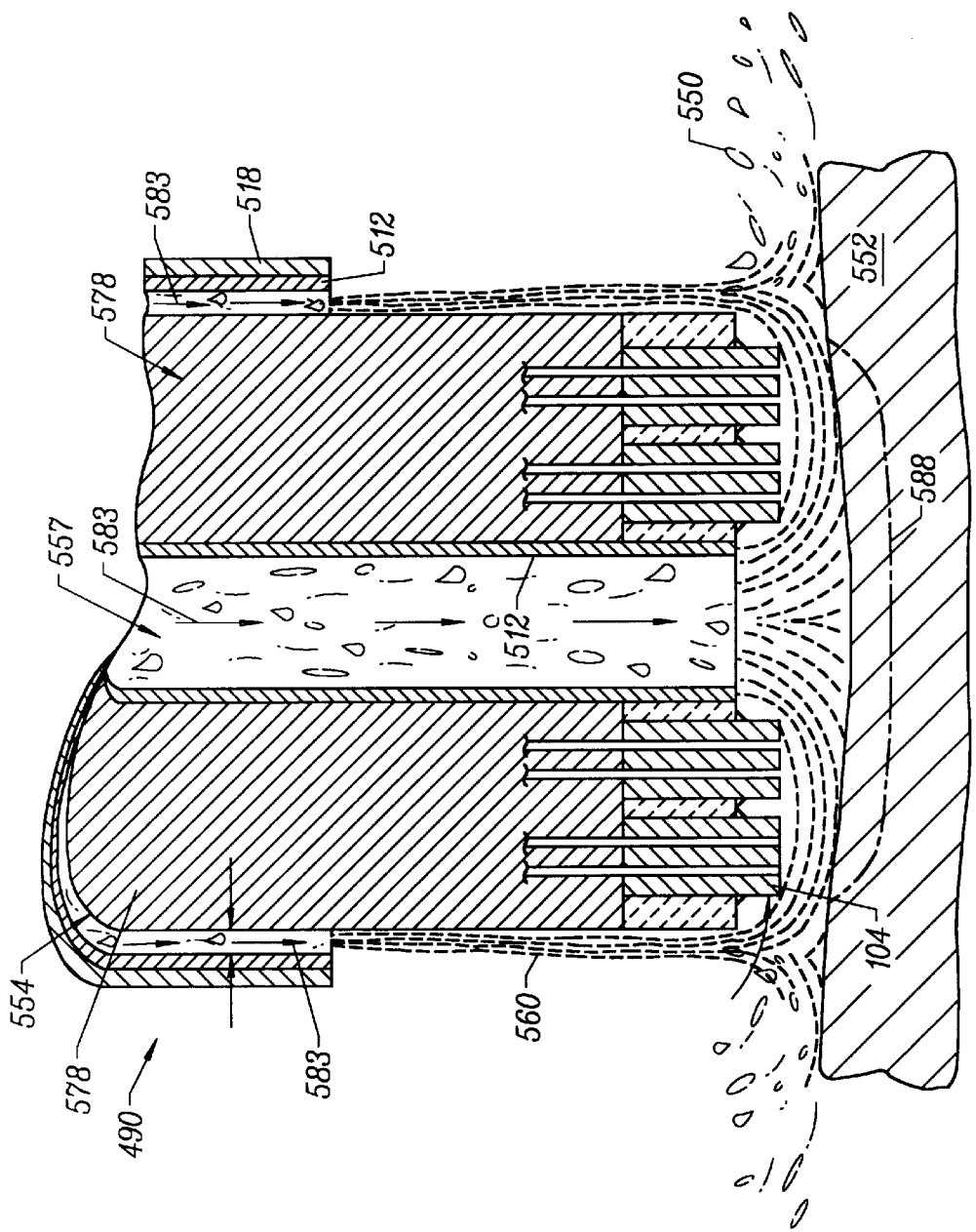

FIGS. 27A–27C schematically illustrate the distal portion of three different embodiments of probe 490 according to the present invention. As shown in 27A, electrode terminals 504 are anchored in a support matrix 502 of suitable insulating material (e.g., ceramic or glass material, such as alumina, silicon nitride zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good thermal shock resistance, good electrically insulative properties, high flexural modulus, resistance to carbon tracking, biocompatibility, and high melting point. The support matrix 502 is adhesively joined to a tubular support member 578 that extends most or all of the distance between matrix 502 and the proximal end of probe 490. Tubular member 578 preferably comprises an electrically insulating material, such as an epoxy or silicone-based material.

In a preferred construction technique, electrode terminals 504 extend through pre-formed openings in the support matrix 502 so that they protrude above tissue treatment surface 512 by the desired distance. The electrodes are then bonded to the tissue treatment surface 512 of support matrix 502, typically by an inorganic sealing material 580. Sealing material 580 is selected to provide effective electrical insulation, and good adhesion to both the alumina matrix 502 and the electrode terminals (e.g., titanium, tungsten, molybdenum, platinum, etc.). Sealing material 580 additionally should have a compatible thermal expansion coefficient and a melting point well below that of the metal electrode terminals and the ceramic support matrix, typically being a glass or glass ceramic.

In the embodiment shown in FIG. 27A, return electrode 512 comprises an annular member positioned around the exterior of shaft 100 of probe 490. Return electrode 512 may fully or partially circumscribe tubular support member 578 to form an annular gap 554 therebetween for flow of electrically conducting fluid 550 therethrough, as discussed below. Gap 554 preferably has a width in the range of 0.1 mm to 4 mm. Alternatively, probe may include a plurality of longitudinal ribs between support member 578 and return electrode 512 to form a plurality of fluid lumens extending along the perimeter of shaft 100. In this embodiment, the plurality of lumens will extend to a plurality of openings.

Return electrode 512 is disposed within an electrically insulative jacket 518, which is typically formed as one or more electrically insulative sheaths or coatings, such as polytetrafluoroethylene, polyamide, and the like. The provision of the electrically insulative jacket 518 over return electrode 512 prevents direct electrical contact between return electrode 512 and any adjacent body structure. Such direct electrical contact between a body structure (e.g., tendon) and an exposed electrode member 512 could result in unwanted heating and necrosis of the structure at the point of contact causing necrosis.

As shown in FIG. 27A, return electrode 512 is not directly connected to electrode terminals 504. To complete this current path so that terminals 504 are electrically connected to return electrode 512, electrically conducting fluid 550 (e.g., isotonic saline) is caused to flow along fluid path(s) 583. Fluid path 583 is formed by annular gap 554 between outer return electrode 512 and tubular support member 578. The electrically conducting fluid 550 flowing through fluid path 583 provides a pathway for electrical current flow between electrode terminals 504 and return electrode 512, as illustrated by the current flux lines 560 in FIG. 6A. When a voltage difference is applied between electrode terminals 504 and return electrode 512, high electric field intensities will be generated at the distal tips of terminals 504 with current flow from terminals 504 through the target tissue to the return electrode, the high electric field intensities causing ablation of tissue 52 in zone 588.

FIG. 27B illustrates another alternative embodiment of electrosurgical probe 490 which has a return electrode 512 positioned within tubular member 578. Return electrode 512 is preferably a tubular member defining an inner lumen 557 for allowing electrically conducting fluid 550 (e.g., isotonic saline) to flow therethrough in electrical contact with return electrode 512. In this embodiment, a voltage difference is applied between electrode terminals 504 and return electrode 512 resulting in electrical current flow through the electrically conducting fluid 550 as shown by current flux lines 560. As a result of the applied voltage difference and concomitant high electric field intensities at the tips of electrode terminals 504, tissue 552 becomes ablated or transected in zone 588.

FIG. 27C illustrates another embodiment of probe 490 that is a combination of the embodiments in FIGS. 27A and 27B. As shown, this probe includes both an inner lumen 557 and an outer gap or plurality of outer lumens 554 for flow of electrically conductive fluid. In this embodiment, the return electrode 512 may be positioned within tubular member 578 as in FIG. 27B, outside of tubular member 578 as in FIG. 27A, or in both locations.

Figure 28:
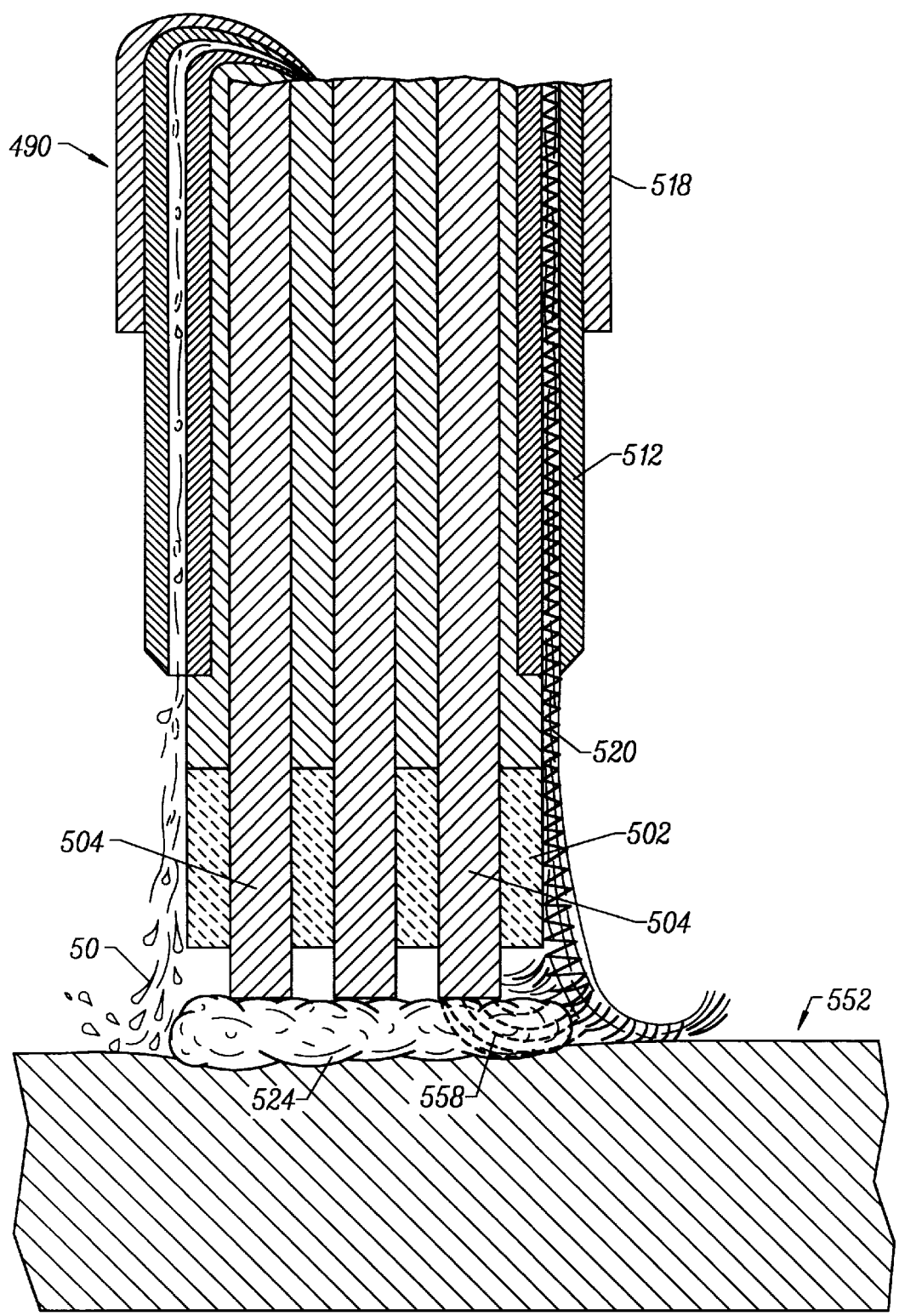
FIG. 28 is a cross-sectional view of the distal tip of the electrosurgical probe, illustrating electric field lines between the active and return electrodes.

FIG. 28 illustrates the current flux lines associated with an electric field 520 applied between the active and return electrodes 504, 512 when a voltage is applied therebetween. As shown, the electric field intensity is substantially higher in the region 588 at the tip of the electrode 504 because the current flux lines are concentrated in these regions. This high electric field intensity leads to induced molecular breakdown of the target tissue through molecular dissociation. As a result of the applied voltage difference between electrode terminal(s) 504 and the target tissue 552 (i.e., the voltage gradient across the plasma layer 524), charged particles (not shown) in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases 526, such as oxygen, nitrogen, carbon dioxide, hydrogen and methane. The short range of the accelerated charged particles within the tissue confines the molecular dissociation process to the surface layer to minimize damage and necrosis to the underlying tissue.

Figure 29:
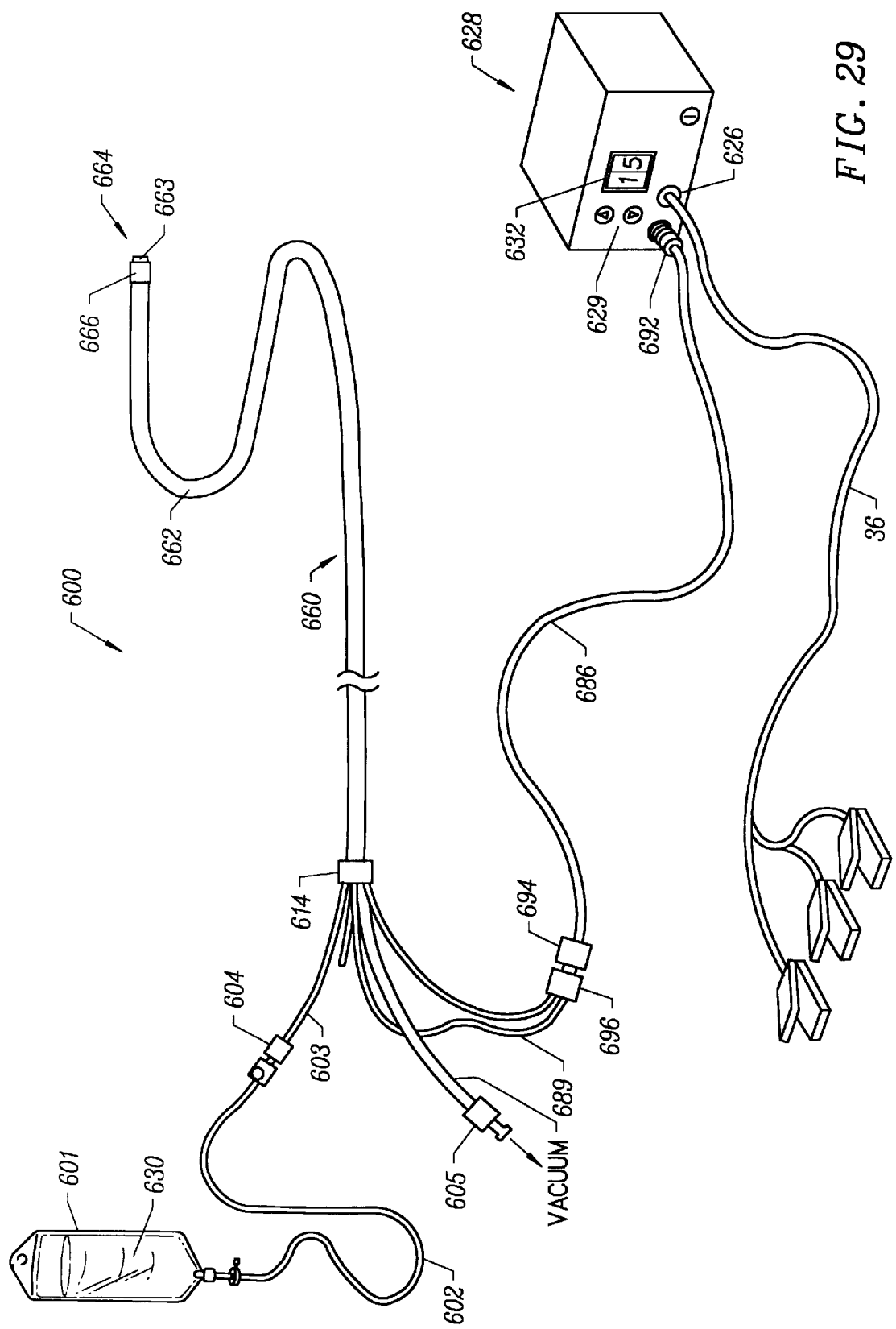
FIG. 29 is a perspective view of an electrosurgical catheter system for removing body structures according to the present invention.

Referring to FIG. 29, the electrosurgical device according to the present invention may also be configured as an elongate catheter system 600 including portions with sufficient flexibility to permit introduction into the body and to the target site through one or more vascular lumen(s). As shown, catheter system 600 generally comprises an electrosurgical catheter 660 connected to a power supply 628 by an interconnecting cable 686 for providing high frequency voltage to a target tissue site and an irrigant reservoir or source 600 for providing electrically conducting fluid to the target site. Catheter 660 generally comprises an elongate, flexible shaft body 662 including a tissue removing or ablating region 664 at the distal end of body 662. The proximal portion of catheter 660 includes a multi-lumen fitment 614 which provides for interconnections between lumens and electrical leads within catheter 660 and conduits and cables proximal to fitment 614. By way of example, a catheter electrical connector 696 is removably connected to a distal cable connector 694 which, in turn, is removably connectable to generator 628 through connector 692. One or more electrically conducting lead wires (not shown) within catheter 660 extend between one or more active electrodes 663 at tissue ablating region 664 and one or more corresponding electrical terminals (also not shown) in catheter connector 696 via active electrode cable branch 687. Similarly, one or more return electrodes 666 at tissue ablating region 664 are coupled to a return electrode cable branch 689 of catheter connector 696 by lead wires (not shown). Of course, a single cable branch (not shown) may be used for both active and return electrodes.

Catheter body 662 may include reinforcing fibers or braids (not shown) in the walls of at least the distal ablation region 664 of body 662 to provide responsive torque control for rotation of electrode terminals during tissue engagement. This rigid portion of the catheter body 662 preferably extends only about 7 to 10 mm while the remainder of the catheter body 662 is flexible to provide good trackability during advancement and positioning of the electrodes adjacent target tissue.

Conductive fluid 630 is provided to tissue ablation region 664 of catheter 660 via a lumen (not shown in FIG. 29) within catheter 660. Fluid is supplied to lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient. A control valve 604 may be positioned at the interface of fluid supply line 602 and conduit 603 to allow manual control of the flow rate of electrically conductive fluid 630. Alternatively, a metering pump or flow regulator may be used to precisely control the flow rate of the conductive fluid.

System 600 further includes an aspiration or vacuum system (not shown) to aspirate liquids and gases from the target site. The aspiration system will usually comprise a source of vacuum coupled to fitment 614 by a aspiration connector 605.

For particular applications, such as for cosmetic surgery on the skin of the patient, it may be desirable to achieve volumetric tissue removal while maintaining relatively low plasma temperatures, e.g., below 100° C., below 80° C., or even below 50° C. This low temperature tissue removal reduces the likelihood of collateral thermal damage to those cells or tissue surrounding the target tissue.

With a lowered vaporization temperature, the energy levels can be reached while decreasing the thermal energy directed to the tissue. One technique for achieving the desired decrease in temperature of volumetric tissue removal is to use an electrically conductive liquid having a vaporization temperature below 100° C., or below 80° C. Applicant believes that the temperature of vaporization into a ionized plasma according to the methods of the present invention is related to the boiling temperature of the liquid. Boiling temperature of a liquid is defined as the temperature of a liquid at which its vapor pressure is equal to or very slightly greater than the atmospheric or external pressure of the environment. As is well known, the boiling temperature of water at sea level (1 atms) is 100° C.

A variety of fluids and/or solutions have boiling temperatures below 100° C. For example, methanol has a boiling temperature of 64.7° C. Preferably, the fluid or solution will comprise an electrically conductive, biocompatible material that is not toxic or harmful to the patient. In addition, for some applications such as arthroscopy, it is further desirable to minimize absorption of the conductive solution into the surrounding tissue cells. It may further be desirable that the liquid solution be an azeotropic. Azeotropic mixtures of two or more substances behave like a single substance in that the vapor produced by partial evaporation of liquid has the same composition as the liquid. This should prevent the uneven depletion of one solution component faster than the other, which may over the course of treatment, undesirably change the boiling temperature.

Figure 31:
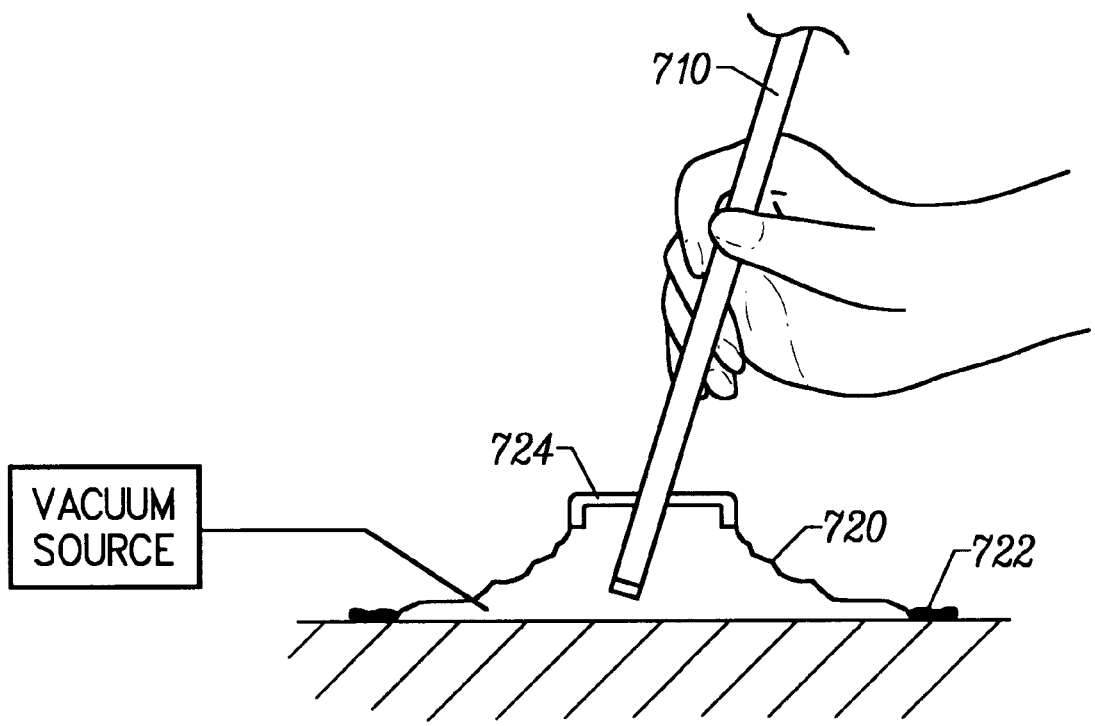
FIG. 31 depicts an electrosurgical probe having a compliant, low pressure chamber according to the present invention.

Another technique for lowering the vaporization temperature of the electrically conductive fluid involves reducing the external vapor pressure of the air or gas near the target site. As illustrated in the chart of FIG. 30, the boiling temperature of water decreases with decreases pressure. Thus, by creating a sub-atmospheric environment in the electrically conductive fluid near the electrode terminal(s), the temperature required for vaporization of the fluid will decrease. In one embodiment shown in FIG. 31, a smaller, compliant chamber or balloon 720 can be attached to the area of the patient to be treated. The compliant chamber 720 has sufficient slack to allow the electrosurgical probe 710 to move freely about the area covered. Adhesive 722 or other attachment devices may be used to secure the chamber 720 to the patient or to the probe. The chamber may comprise a material such as glass or a transparent polymer that allows for clear viewing of the working end of the probe 710. Alternatively, the chamber 720 may include a clear, hardened portion 724 that also functions to maintain the slack in the chamber 720 away from the working end of the probe 710. The hardened portion 724 may assume a variety of shapes such as dome, cylindrical, circular, and the like.

When the electrode terminal(s) are activated in a saline solution according to the present invention, the ions in the plasma typically fluoresce with a yellow-orange color. It is believed that the color results from the excitation of the ionic particles as they are accelerated towards the target tissue. The color of the fluorescence at least partly depends on the ionic material included in the solution, as illustrated in FIG. 32. In some embodiments of the present invention, it is preferred that the fluorescence color comprise blue, green, purple or another color that is not generally associated with conventional electrosurgical arcing or other thermal processes. It may be further desirable to simulate the color of excimer laser light to reassure the patient and user that the process involves cold ablation mechanisms. Accordingly, those compounds having potassium, copper, and barium may be selected. In particular, applicant has found that solutions of potassium chloride (in the range of about 0.5 to 5%) provide a purple-blue color that appears cooler than the orange-yellow color of saline, which is often associated with conventional electrosurgical arcing.

Preferably, the material used will have ionizing qualities similar to the sodium chloride used in saline solutions. The concentration of these materials will be varied depending on the strength of volumetric tissue removal desired. Furthermore, spectrophotometric analysis of the plasma created using a saline solution reversal is a broad peak near 308 nm (same wavelength as the XeCl excimer laser) and a yet higher peak intensity at 588 nm (giving rise to the yellow/orange color of the saline plasma). With the proper selection of metal salts or ionic material, more of the wavelength may be concentrated near the 308 nm wavelength of the excimer laser.

Applicant has found that increasing the current densities around the electrode terminal(s) can lead to higher energy levels in the ionized plasma. This, in turn, allows the ionized plasma to break stronger molecular bonds, such as those present in bone or calcified fragments. Since the electrically conductive fluid between the target site and electrode terminal(s) is transformed into an ionized vapor layer or plasma, the number of charged particles which can be accelerated against the target also determines the removal rate. In addition, the conductivity of the fluid may have an effect on the strength of the plasma field created at the end of the probe. Typically, isotonic saline with 0.9% concentration of sodium chloride is used with the probe. By increasing the sodium chloride concentration to greater than 0.9% and preferably between about 3% and 20%, the increased concentration provides for improved tissue ablation rates. This concept of using a hypertonic saline with enhanced conductivity and increased numbers of charged particles is of particular use in bone removal processes or in other procedures requiring aggressive volumetric removal.

Applicant has also found that the plasma layer typically requires a higher voltage level to initiate a plasma than to sustain the plasma once it has been initiated. In addition, it has been found that some conductive solutions facilitate the initiation of the plasma layer, rather than the energy level of the plasma, as discussed above. For example, it has been found that saline solutions having concentrations less than isotonic saline (i.e., less than 0.9% sodium chloride) facilitate the initiation of the plasma layer. This may be useful in applications where initiation of the plasma layer is more difficult, such as applications where a suction pressure is applied near the electrode terminal(s). A more complete description of this type of application, and the devices that carry out simultaneous suction and ablation can be found in U.S. patent application Ser. No. 09/010,382, filed Jan. 21, 1998 (Attorney Docket No. A-6), the complete disclosure of which is incorporated herein by reference for all purposes.

In another embodiment, the active electrodes are spaced from the tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

Figure 33:
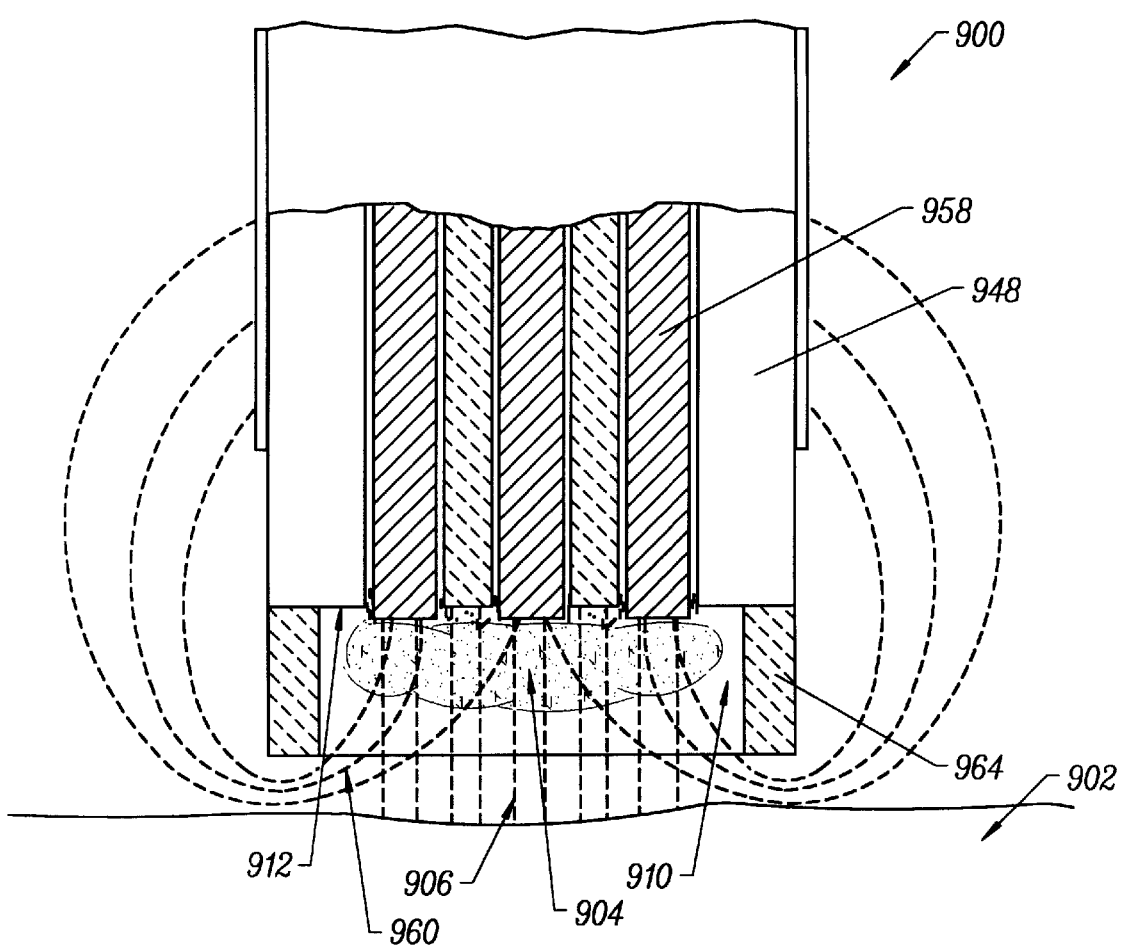
FIG. 33 illustrates an electrosurgical probe having electrode terminals recessed within a plasma chamber at the distal end of the probe.

FIG. 33 illustrates the working end of electrosurgical probe 900 having a plurality of electrode terminals 958 recessed from a distal surface 960 of an insulating support member 948 to prevent contact between electrode terminals 958 and the tissue 902. Preferably, electrode terminals 958 will be spaced a sufficient distance to prevent direct contact between the vapor layer 904 formed around terminals 958 and the tissue 902, while allowing ions 906 from the vapor layer 904 to reach the tissue 902 for the ablation process described above. This distance will vary with the voltage applied, the electrode configurations, the ionic concentration of the conductive fluid and other factors. In the representative embodiment, the electrode terminals 958 are spaced a distance of about 1.0 mm to 5.0 mm, preferably about 2.0 mm, from distal surface 960, and the applied voltage is about 200 to 300 volts rms or about 400 to 600 volts peak to peak (with a square waveform). In this embodiment, the conductive fluid is isotonic saline, which has a sodium chloride concentration of about 0.9%. Applicant has found that increasing the concentration of sodium chloride or increasing the voltage applied between the electrode terminals and the return electrode allows use of a higher voltage level. Applicant has further found that a higher voltage level and more concentration ionic fluid will increase the concentration and energy level of the ions within the plasma. By increasing the distance between the electrode terminals and the tissue, a higher rate of ablation can be achieved without increasing (and in some instances actually decreasing) the temperature at the tissue level.

As shown in FIG. 33, support member 948 includes an annular extension 964 that extends distally from the electrode terminals 958 and the inner portion 912 of support member 948. Annular extension 964 will preferably comprises an electrically insulating material, such as a ceramic or glass composition, and it may comprise a transparent material that allows the physician to view the plasma chamber 910 formed therein. In the representative embodiment, the electrode terminals 958 extend distally from the inner portion 912 of support member 948. This configuration increases the current densities near the edges of electrode terminals 948 to increase the strength of the plasma 904 and the rate of ablation while still maintaining a space between the electrode terminals 948 and the distal surface 960 of annular extension 964. In this embodiment, a return electrode 920 is positioned proximally of electrode terminals 958, and outside of plasma chamber 910. However, the return electrode 920 may also be positioned within plasma chamber 910 if it is desired to confine the electric current to the plasma chamber 910. In this latter configuration, the return and active electrodes will be suitable configured and spaced to avoid current shorting therebetween.

In the representative embodiment, probe 900 is used in a wet field, or one that is already immersed in conductive fluid. However, it will be recognized that this embodiment may also be used in a dry field, wherein the conductive fluid is supplied to the target site, e.g., via a fluid lumen or tube within the probe. Preferably, the fluid tube(s) will have distal opening(s) within the plasma chamber 910 to allow for continual resupply of conductive fluid around electrode terminals 958 even if the surgeon presses the probe against the tissue, which reduces collateral damage to the tissue. In another embodiment (not shown), the probe will include an aspiration lumen (not shown) having a distal opening with the plasma chamber 910 such that excess fluid within the cavity is immediately aspirated through the lumen. This configuration, together with a return electrode positioned within the plasma chamber 910, allows the physician to create a closed fluid and electric circuit that minimizes fluid and current leakage outside of the plasma chamber 910.

In another embodiment, a screen made of a suitable material that will allow passage of vapor or the plasma layer while substantially preventing passage of fluid, such as a synthetic material mesh, closes the distal opening of the plasma chamber, minimizing the amount of fluid leaking out of the chamber, without significantly restraining the plasma field.

What is claimed is:

1. A method for applying electrical energy to tissue comprising:

positioning an active electrode adjacent to or in contact with tissue in the presence of electrically conductive fluid;

applying a sufficient high frequency voltage difference between the electrode terminal and a return electrode to generate a plasma adjacent to the active electrode; and effecting ablation of at least a portion of the tissue.

2. The method of claim 1 further comprising generating electric fields adjacent the active electrode, the electric fields having sufficient energy to generate the plasma.

3. The method of claim 1 further comprising vaporizing a portion of the electrically conductive fluid adjacent to the active electrode.

4. The method of claim 1 wherein the effecting ablation step is carried out by contacting the tissue with the plasma.

5. The method of claim 1 wherein the effecting ablation step is carried out by generating the plasma at a location spaced from the tissue.

6. The method of claim 5 wherein the plasma is generated at a location spaced a distance of about 0.05 to 5 mm from the tissue, the method further comprising the step of accelerating ions from the plasma such that the ions contact the tissue.

7. The method of claim 1 further comprising positioning the return electrode within the electrically conductive fluid such that electrically conductive fluid forms a current flow path between the active and return electrodes.

8. The method of claim 1 further comprising directing the electrically conductive fluid along a fluid path in contact with the active and return electrodes.

9. The method of claim 1 further comprising applying a sufficient high frequency voltage difference between the active and return electrodes to generate energy of at least 3.5 eV within or around the plasma.

10. The method of claim 1 further comprising applying a sufficient high frequency voltage difference between the active and return electrodes to generate energy of at least 4.0 eV within or around the plasma.

11. A method for applying electrical energy to tissue comprising:

positioning an active electrode adjacent to or in contact with tissue in the presence of electrically conductive fluid;

applying a sufficient high frequency voltage difference between the electrode terminal and a return electrode to vaporize a portion of the electrically conductive fluid such that the vaporized fluid has a temperature below 100° C.; and effecting ablation of at least a portion of the tissue in contact with the vaporized fluid .

12. The method of claim 11 wherein the electrically conductive fluid is vaporized at a subatmospheric pressure.

13. The method of claim 11 wherein said electrically conductive fluid has a boiling temperature below 100° C. at 1 atmosphere pressure.

14. The method of claim 11 further comprising applying a sufficient high frequency voltage difference between the active and return electrodes to generate energy of at least 3.5 eV within or around the vaporized fluid.

15. The method of claim 11 further comprising applying a sufficient high frequency voltage difference between the active and return electrodes to generate energy of at least 4.0 eV within or around the vaporized fluid.

16. The method of claim 11 further comprising applying a sufficient high frequency voltage difference between the electrode terminal and a return electrode to vaporize a portion of the electrically conductive fluid such that the vaporized fluid has a temperature below about 80° C.

17. A method for applying electrical energy to tissue comprising: positioning an active electrode adjacent to or in contact with tissue in the presence of an electrically conductive fluid comprising at least about 1.0% sodium chloride;

applying a sufficient high frequency voltage difference between the electrode terminal and a return electrode to vaporize a portion of the electrically conductive fluid; and effecting ablation of at least a portion of the tissue in contact with the vaporized fluid.

18. The method of claim 17 wherein the electrically conductive fluid comprises at least about 2% sodium chloride.

19. The method of claim 17 wherein the electrically conductive fluid comprises at least about 5% sodium chloride.

20. A method for applying electrical energy to tissue comprising:

positioning an active electrode adjacent to or in contact with tissue in the presence of an electrically conductive fluid comprising between about 0.1% to 0.85% sodium chloride;

applying a sufficient high frequency voltage difference between the electrode terminal and a return electrode to vaporize a portion of the electrically conductive fluid; and effecting ablation of at least a portion of the tissue in contact with the vaporized fluid.

21. A method for applying electrical energy to tissue comprising:

positioning an active electrode near tissue in the presence of electrically conductive fluid;

applying a sufficient high frequency voltage difference between the electrode terminal and a return electrode to generate a plasma adjacent to the active electrode; and effecting ablation of at least a portion of the tissue, while maintaining the active electrode at least 1.0 mm away from the tissue.

22. The method of claim 21 further comprising effecting ablation of at least a portion of the tissue, while maintaining the active electrode at least 2.0 mm away from the tissue.

* * * * *